US012398403B2

United States Patent
Godia-Casablancas et al.

(10) Patent No.: US 12,398,403 B2
(45) Date of Patent: Aug. 26, 2025

(54) METHODS FOR THE MANUFACTURE OF RECOMBINANT VIRAL VECTORS

(71) Applicants: ESTEVE PHARMACEUTICALS, S.A., Barcelona (ES); UNIVERSITAT AUTÓNOMA DE BARCELONA, Cerdanyola del Vallès (ES)

(72) Inventors: Francesc Godia-Casablancas, Sabadell (ES); Maria-Fàtima Bosch-Tubert, Cerdanyola del Vallès (ES); Miguel Garcia-Martinez, Terrassa (ES); Laura Cervera-Gracia, Barcelona (ES); Xavier Leon-Madrenas, Sant Feliu de Guixols (ES); Maria Molas-Laplana, Barcelona (ES); Sonia Gutierrez-Granados, Sabadell (ES)

(73) Assignees: ESTEVE PHARMACEUTICALS, S.A., Barcelona (ES); UNIVERSITAT AUTÓNOMA DE BARCELONA, Cerdanyola del Vallès (ES)

( * ) Notice: Subject to any disclaimer, the term of this patent is extended or adjusted under 35 U.S.C. 154(b) by 885 days.

(21) Appl. No.: 17/598,503

(22) PCT Filed: Mar. 26, 2020

(86) PCT No.: PCT/EP2020/058527
§ 371 (c)(1),
(2) Date: Sep. 27, 2021

(87) PCT Pub. No.: WO2020/193698
PCT Pub. Date: Oct. 1, 2020

(65) Prior Publication Data
US 2022/0186255 A1 Jun. 16, 2022

(30) Foreign Application Priority Data
Mar. 28, 2019 (EP) .................................... 19382220

(51) Int. Cl.
*C12N 15/80* (2006.01)
*C12N 7/02* (2006.01)
*C12N 15/86* (2006.01)

(52) U.S. Cl.
CPC ............. *C12N 15/86* (2013.01); *C12N 7/02* (2013.01); *C12N 2750/14143* (2013.01); *C12N 2750/14152* (2013.01)

(58) Field of Classification Search
CPC .......... C12N 15/86; C12N 2750/14143; C12N 2750/14152; C12N 7/02

USPC ...................................................... 435/320.1
See application file for complete search history.

(56) References Cited

U.S. PATENT DOCUMENTS 5,622,856 A 4/1997 Natsoulis

FOREIGN PATENT DOCUMENTS

| EP | 3101125 | 12/2016 |
| WO | WO2011154520 | 12/2011 |
| WO | WO2014144486 | 9/2014 |

OTHER PUBLICATIONS

Kisselev L., (Structure, 2002, vol. 10: 8-9.*
Witkowski et al., (Biochemistry 38:11643-11650, 1999.*
Whisstock et al., (Quarterly Reviews of Biophysics 2003, vol. 36 (3): 307-340.*
Devos et al., (Proteins: Structure, Function and Genetics, 2000, vol. 41: 98-107.*
Alexopoulos, Annika, N., et al., "The CMV early enhancer/chicken β actin (CA6) promoter can be used to drive transgene expression during the differentiation of murine embryonic stem cells into vascular progenitors", BMC Cell Biology, www.biomedcentral.com/1471-212/9/2.
Aponte-Ubillus, Juan Jose, et al., "Molecular design for recombinant adeno-associated virus (rAAV) vector production", Applied Microbiology and Biotechnology, vol. 102, 2017, pp. 1045-1054.
Ayuso, E, et al., "High AAV vector purity results in serotype- and tissue-independent enhancement of transduction efficiency", Gene Therapy, 17, 2010, pp. 503-510.
Cervera, Laura, et al., "Extended gene expression by medium exchange and repeated transtext transfection for recombinant protein production enhancement", Biotechnology and Bioengineering, vol. 112: 1-13, 2015.
Grieger, Jostiva, C., et al., "Production of recombinant adeno-associated virus vectors using suspension HEK293 cells and continuous harvest of vector from the culture media for GMP FIX and FLTI clinical vector", Molecular Therapy, vol. 24, pp. 287-297, 2016.
Grimm, Dirk, "Production methods for gene transfer vectors based on adeno-associated virus serotypes", Methods, Academic Press, vol. 28(2), pp. 146-157, 2002.
International Search Report for PCT/EP2020/058527 dated May 26, 2020.
Niwa, Hitosti, et al., "Efficient selection for high-expression a novel eukaryotic vector", Gene, vol. 108, 1991, pp. 193-200.

(Continued)

*Primary Examiner* — Robert B Mondesi
*Assistant Examiner* — Mohammad Y Meah
(74) *Attorney, Agent, or Firm* — HUESCHEN AND SAGE

(57) ABSTRACT

The present invention relates to methods for the production of high titer recombinant viral vectors, more particularly recombinant AAV vectors, so that the methods can be effectively employed on a scale that is suitable for the practical application of gene therapy techniques.

10 Claims, 7 Drawing Sheets

Specification includes a Sequence Listing.

(56) References Cited

OTHER PUBLICATIONS

Reed, Sharon, E., et al., "Transfaction of mammalian cells using linear polyethylanimine is a simple and effective means of producing recombinant adeno-associated virus vectors", Journal of Virological Methods, 138, 2006, pp. 85-98.

Sharon, David, et al., "Advancements in the design and scalable production of viral gene transfer vectors", Biotechnology and Bioengineering, 115, 2018, pp. 25-40.

Xiao, Xiao, et al., "Production of high-titer recombinant adeno-associated virus vectors in the absence of helper adenovirus", Journal of Virology, 72:2224-2232, 1998.

* cited by examiner

METHODS FOR THE MANUFACTURE OF RECOMBINANT VIRAL VECTORS

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 73,728 Bytes ASCII (Text) file named "SEQUENCE_LISTING.TXT," created on 16 Sep. 2021.

FIELD OF THE INVENTION

The present invention relates to methods for the production of high titer recombinant viral vectors, more particularly recombinant AAV vectors, so that the methods can be effectively employed on a scale that is suitable for the practical application of gene therapy techniques.

BACKGROUND OF THE INVENTION

Gene delivery is a promising method for the treatment of acquired and inherited diseases. A number of viral-based systems for gene transfer purposes have been described, including Adeno-Associated Virus (AAV)-based systems.

AAVs have unique features that make them attractive as vectors for gene therapy. AAV infect a wide range of cell types. However, they are non-transforming, and are not implicated in the etiology of any human disease. Introduction of DNA to recipient host cells generally leads to long-term persistence and expression of the DNA without disturbing the normal metabolism of the cell.

AAV particles are comprised of a proteinaceous capsid having three capsid proteins, VP1, VP2 and VP3, which enclose a ~4.7 kb linear single-stranded DNA genome containing the Rep and Cap genes flanked by the viral inverted terminal repeats (ITRs). Individual particles package only one DNA molecule strand, but this may be either the plus or minus strand. Particles containing either strand are infectious, and replication occurs by conversion of the parental infecting single strand to a duplex form, and subsequent amplification, from which progeny single strands are displaced and packaged into capsids.

AAV vectors can be engineered to carry a heterologous nucleotide sequence of interest (e.g., a selected gene, antisense nucleic acid molecule, ribozyme, or the like) by deleting the internal portion of the AAV genome and inserting the DNA sequence of interest between the ITRs. The ITRs are the only sequences required in cis for replication and packaging of the vector genome containing the heterologous nucleotide sequence of interest. The heterologous nucleotide sequence is also typically linked to a promoter sequence capable of driving gene expression in the patient's target cells under certain conditions. Termination signals, such as polyadenylation sites, are usually included in the vector.

The rep and cap AAV gene products provide functions for replication and encapsidation of the vector genome, respectively, and it is sufficient for them to be present in trans.

Despite the potential benefits of gene therapy as a treatment for human genetic diseases, serious practical limitations stand in the way of its widespread use in the clinic. In this sense, it is necessary to produce big amounts of rAAV particles in order to produce clinically effective doses. Production of a large number of particles using current technology requires a large number of producer cells. At a laboratory scale, it would require thousands of tissue culture flasks. At a commercial scale, more efficient and intensive production platforms are needed to reach clinical application. The benefits of improving both, the number of producing cells and the particle yield per cell, will be very significant from a commercial production standpoint.

Accordingly, in the development of recombinant AAV vectors such as those for use in gene therapy, there is a need for strategies that achieve a high titer of AAV so that the methods can be effectively employed on a scale that is suitable for the practical application of gene therapy techniques.

The present disclosure provides methods for achieving these competing goals and demonstrates that such techniques can be employed for the large-scale production of recombinant AAV vector preparations.

SUMMARY OF THE INVENTION

The inventors of the present invention have found that, surprisingly, recombinant viral production, more particularly rAAV production, can be significantly improved by performing repeated transfections. As it is shown in the Examples below, a sustained level of gene expression over time is obtained when repeated rounds of transfection are performed, as opposed to the conventional approach which entails a single transfection round.

Thus, in a first aspect, the invention refers to a method for the production of a recombinant viral vector said method comprising the steps of:
 a) co-transfecting a suitable cell culture with at least two plasmid vectors, said plasmid vectors comprising a heterologous nucleotide sequence and replication and packaging gene sequences;
 b) culturing said cells under conditions allowing viral replication and packaging;
 c) recovering the viral vectors produced in step b) and retaining the cells in the cell culture under conditions allowing further division and growth;
 d) re-transfecting the cells according to step c) with the plasmid vectors according to step a); and
 e) repeating steps b) to c).

Furthermore, the inventors have found that the combination of optimized plasmids for the transfection, results in higher yield of rAAV than production with the standard plasmids commonly used for AAV vector production. Moreover, as it is shown in the Examples below, the inventors have surprisingly found that the use of the optimized plasmids according to the invention results in lower reverse packaging of bacterial sequences.

It is thus a further aspect of the present invention a method for h production of a recombinant AAV said method comprising the steps of:
 a) co-transfecting a suitable cell with
  i) a first plasmid vector comprising a heterologous nucleoli sequence flanked by ITRs;
  ii) a second plasmid vector comprising from 5' to 3' an AAV rep coding region, an AAV cap coding region and a nucleotide sequence comprising an AAV p5 promoter region, and
  iii) a third plasmid vector comprising adenovirus helper functions including VA-RNA, E2A and E4 sequences, wherein said plasmid does not contain E3, pTB (E2B), Ad ITR and protease sequences;
 b) culturing said cell under conditions allowing AAV replication and packaging; and
 c) recovering the AAVs produced in step b).

The inventors have surprisingly found that by using a combination of optimized plasmids in the transfection, reverse packaging is greatly reduced and higher vector genome yield is obtained.

Thus, in another aspect, the invention refers to a plasmid vector comprising:
a) a heterologous nucleotide sequence flanked by ITRs; and
b) a stuffer DNA sequence located outside said ITRs and adjacent to one ITR, wherein said stuffer sequence has a length between 4400 Kb and 4800 Kb so that the plasmid backbone size is above 5 Kb, preferably between 7000 bp and 7500 bp;

wherein said plasmid vector does not contain a F1Ori nucleotide sequence in the backbone sequence.

In a further aspect, the invention refers to a plasmid vector comprising adenovirus helper functions including VA-RNA, E2A and E4 sequences, wherein said plasmid does not contain E3, pTB(E2B), and Ad ITR protease sequences.

DEPOSIT OF MICROORGANISMS

Figure 1:
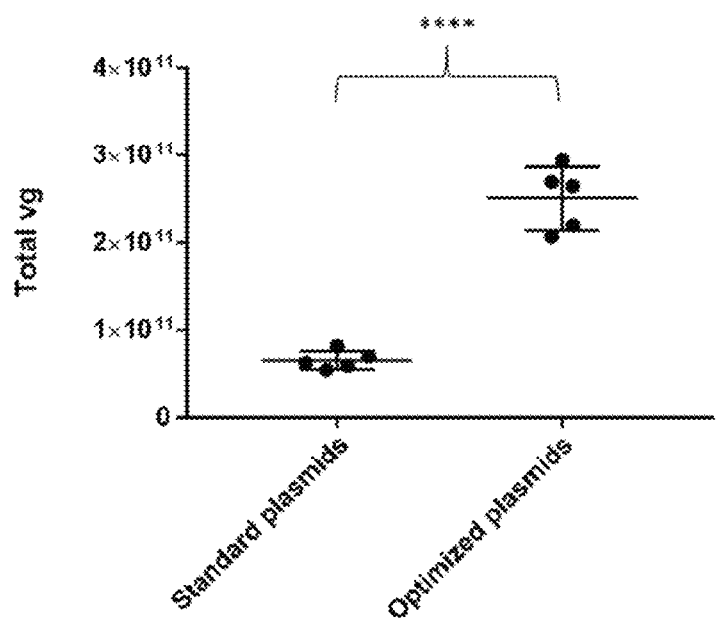
FIG. 1. Yields of AAV9-CAG-cohSgsh expressed in total vg produced by triple transfection with a set of standard plasmids or a set of optimized plasmids.

The plasmid pAdHelper861 was deposited on Dec. 5, 2018, under access number DSM 32965 at the DSMZ—Deutsche Sammlung von Mikroorganismen und Zeilkulturen, Inhoffenstraße 7 B, D-38124 Braunschweig, Federal Republic of Germany.

The plasmid pcohSgsh-827 was deposited on Dec. 5, 2018, under access number DSM 32966 at the DSMZ—Deutsche Sammlung von Mikroorganismen and Zellkulturen, Inhoffenstraße 7 B, D-38124 Braunschweig, Federal Republic of Germany.

The plasmid pcohSgsh-900 was deposited on Dec. 5, 2018, under access number DSM 32967 at the DSMZ—Deutsche Sammlung von Mikroorganismen und Zellkulturen, Inhoffenstraße 7 B, D-38124 Braunschweig, Federal Republic of Germany.

The plasmid pohIDS-874 was deposited on Dec. 5, 2018, under access number DSM 32968 at the DSMZ—Deutsche Sammlung von Mikroorganismen und Zellkulturen, Inhoffenstraße 7 B, D-38124 Braunschweig, Federal Republic of Germany.

The plasmid pRepCap9-809 was deposited on Dec. 5, 2018, under access number DSM 32969 at the DSMZ—Deutsche Sammlung von Mikroorganismen und Zellkulturen, Inhoffenstraße 7 B, D-38124 Braunschweig, Federal Republic of Germany.

Definitions

A "vector" as used herein refers to a macromolecule or association of macromolecules that comprises or associates with a polynucleotide and which can be used to mediate delivery of the polynucleotide to a cell. Illustrative vectors include, for example, plasmids, viral vectors, liposomes and other gene delivery vehicles.

The terms "adeno-associated virus", "AAV virus", "AAV virion," "AAV viral particle" and "AAV particle", used as synonyms herein, refer to a viral particle composed of at least one capsid protein of AAV (preferably composed of all capsid proteins of a particular AAV serotype) and an encapsulated polynucleotide corresponding to the AAV genome. The wild-type AAV refers to a virus that belongs to the genus Dependovirus, family Parvoviridae. The wild-type AAV genome is approximately 4.7 Kb in length and consists of a single stranded deoxyribonucleic acid (ssDNA) that can be positive or negative-sensed. The wild-type genome includes inverted terminal repeats (ITR) at both ends of the DNA strand, and three open reading frames (ORFs). The ORF rep encodes for four Rep proteins necessary for AAV lifecycle. The ORF cap contains nucleotide sequences encoding capsid proteins: VP1, VP2 and VP3, which interact to form a capsid of icosahedral symmetry. Finally, the AAP ORF, which overlaps with the Cap ORF, encodes for the AAP protein that appears to promote capsid assembly. If the particle comprises a heterologous polynucleotide (i.e. a polynucleotide different from a wild-type AAV genome, such as a transgene to be delivered to a mammalian cell) flanked by AAV ITRs, then it is typically known as "AAV vector particle" or "AAV viral vector" or "AAV vector" or "recombinant AAV vectors". The invention also encompasses the use of double stranded AAV or self-complimentary AAV, also called dsAAV or scAAV.

The term "adeno-associated virus ITRs" or "AAV ITRs", as used herein, refers to the inverted terminal repeats present at both ends of the DNA strand of the genome of an AAV. The ITR sequences are required for efficient multiplication of the AAV genome. Another property of these sequences is their ability to form a hairpin. This characteristic contributes to their self-priming, which allows the primase-independent synthesis of the second DNA strand. The ITRs have also been shown to be required for both integration of the wild-type AAV DNA into the host cell genome (e.g. in the human $19^{th}$ chromosome for serotype 2 MV) and rescue from it, as well as for efficient encapsidation of the MV DNA into a fully assembled, deoxyribonuclease-resistant AAV particle. The ITR sequences are about 145 bp in length. Preferably, the entire sequences of the ITRs are used in the genome of the AAV viral vector, although some degree of minor modification of these sequences is permissible. A wild-type ITR sequence may be altered by insertion, deletion or truncation, as long as the ITR mediates the desired functions, e.g. replication, nicking, virus packaging, integration, and/or provirus rescue. Procedures for modifying these ITR sequences are well known in the art. The ITR may be from any wild-type AAV, including but not limited to serotypes 1, 2, 3, 4, 5, 6, 7, 8, 9, 10, 11 or 12 or any other AAV known or later discovered. The AAV comprises two ITRs, which may be the same or different. Further, the two AAV ITRs can be from the same AAV serotype as the AAV capsid, or can be different. In a preferred embodiment, the 5' and 3' AAV ITRs derive from AAV1, AAV2, AAV4, AAV5, AAV7, AAV8 and/or AAV9. Preferably ITRs are from AAV2, AAV8 and/or AAV9 being AAV2 the most preferred. In one embodiment, the AAV2 ITRs are selected to generate a pseudotyped AAV (i.e. an AAV having capsid and ITRs derived from different serotypes).

The expression "recombinant viral genome", as used herein, refers to an MV genome in which at least one extraneous polynucleotide is inserted into the naturally occurring AAV genome. The genome of the AAV according to the invention typically comprises the cis-acting 5' and 3' inverted terminal repeat sequences (ITRs) and an expression cassette. A "rAAV vector" as used herein refers to an AAV vector comprising a polynucleotide sequence not of AAV origin (i.e., a polynucleotide heterologous to AAV), typically a sequence of interest for the genetic transformation of a cell. In preferred vector constructs of this invention, the heterologous polynucleotide is flanked by two AAV inverted terminal repeat sequences (ITRs).

An "AAV virus" or "AAV viral particle" refers to a viral particle composed of at least one AAV capsid protein (preferably by all of the capsid proteins of a wild-type AAV) and an encapsidated polynucleotide. If the particle comprises a heterologous polynucleotide (i.e. a polynucleotide other than a wild-type AAV genome such as a transgene to be delivered to a mammalian cell), it is typically referred to as a "rAAV vector particle" or simply a "rAAV vector".

"Packaging" refers to a series of intracellular events that result in the assembly of the capsid proteins and encapsidation of the vector genome to form an AAV particle.

AAV "rep" and "cap" genes refer to polynucleotide sequences encoding replication and encapsidation proteins of adeno-associated virus. They have been found in all AAV serotypes examined, and are described below and in the art. AAV rep and cap are referred to herein as AAV "packaging genes".

The term "GAG promoter" refers to the combination formed by the cytomegalovirus early enhancer element, chicken β-actin promoter and 3' splice sequence derived from the rabbit beta-globin gene (See Alexopoulou A, et al., BMC Cell Biology 2008; 9(2): 1-11, Niwa et al, Gene. 1991 Dec. 15; 108(2):193-9).

The term "polynucleotide" refers to a polymeric form of nucleotides of any length, including deoxyribonucleotides or ribonucleotides, or analogs thereof. A polynucleotide may comprise modified nucleotides, such as methylated nucleotides and nucleotide analogs, and may be interrupted by non-nucleotide components. If present, modifications to the nucleotide structure may be imparted before or after assembly of the polymer. The term polynucleotide, as used herein, refers interchangeably to double- and single-stranded molecules. Unless otherwise specified or required, any embodiment of the invention described herein that is a polynucleotide encompasses both the double-stranded form and each of two complementary single-stranded forms known or predicted to make up the double-stranded form.

A "gene" refers to a polynucleotide containing at least one open reading frame that is capable of encoding a particular protein after being transcribed and translated, or polynucleotide containing at least one non-coding RNA.

The term "nucleotide sequence" refers to a nucleic acid molecule, either DNA or RNA, containing deoxyribonucleotides or ribonucleotides. The nucleic acid may be double stranded, single stranded, or contain portions of both double stranded or single stranded sequence.

The term "codify" refers to the genetic code that determines how a nucleotide sequence is translated into a polypeptide, or a protein. The order of the nucleotides in a sequence determines the order of amino acids along a polypeptide or a protein.

"Recombinant", as applied to a polynucleotide, means that the polynucleotide is the product of various combinations of cloning, restriction or ligation steps, and other procedures that result in a construct that is distinct from a polynucleotide found in nature. A recombinant virus is a viral particle comprising a recombinant polynucleotide. The terms respectively include replicates of the original polynucleotide construct and progeny of the original virus construct.

A "control element" or "control sequence" is a nucleotide sequence involved in an interaction of molecules that contributes to the functional regulation of a polynucleotide, including replication, duplication, transcription, splicing, translation, or degradation of the polynucleotide. The regulation may affect the frequency, speed, or specificity of the process, and may be enhancing or inhibitory in nature. Control elements known in the art include, for example, transcriptional regulatory sequences such as promoters and enhancers. A promoter is a DNA region capable under certain conditions of binding RNA polymerase and initiating transcription of a coding region usually located downstream (in the 3' direction) from the promoter.

"Operatively linked" or "operably linked" refers to a juxtaposition of genetic elements, wherein the elements are in a relationship permitting them to operate in the expected manner. For instance, a promoter is operatively linked to a coding region if the promoter helps to initiate transcription of the coding sequence. There may be intervening residues between the promoter and coding region so long as this functional relationship is maintained.

An "expression vector" is a vector comprising a region, which encodes a polypeptide of interest, and is used for effecting the expression of the protein in an intended target cell. An expression vector also comprises control elements operatively linked to the encoding region to facilitate expression of the protein in the target. The combination of control elements and a gene or genes to which they are operably linked for expression is sometimes referred to as an "expression cassette," a large number of which are known and available in the art or can be readily constructed from components that are available in the art.

"Heterologous" means derived from a genotypically distinct entity from that of the rest of the entity to which it is being compared. For example, a polynucleotide introduced by genetic engineering techniques into a plasmid or vector derived from a different species is a heterologous polynucleotide. A promoter removed from its native coding sequence and operatively linked to a coding sequence with which it is not naturally found linked is a heterologous promoter. In particular, the term "heterologous nucleotide sequence" as used herein includes coding as well as non-coding nucleotide sequences.

"Genetic alteration" refers to a process wherein a genetic element is introduced into a cell other than by mitosis or meiosis. The element may be heterologous to the cell, or it may be an additional copy or improved version of an element already present in the cell. Genetic alteration may be effected, for example, by transfecting a cell with a recombinant plasmid or other polynucleotide through any process known in the art, such as electroporation, calcium phosphate precipitation, or contacting with a polynucleotide-liposome complex. Genetic alteration may also be effected, for example, by transduction or infection with a DNA or RNA virus or viral vector. Preferably, the genetic element is introduced into a chromosome or mini-chromosome in the cell; but any alteration that changes the phenotype and/or genotype of the cell and its progeny is included in this term.

The terms "polypeptide", "peptide" and "protein" are used interchangeably herein to refer to polymers of amino acids of any length. The terms also encompass an amino acid polymer that has been modified; for example, disulfide bond formation, glycosylation, lipidation, or conjugation with a labeling component.

An "isolated" plasmid, virus, or other substance refers to a preparation of the substance devoid of at least some of the other components that may also be present where the substance or a similar substance naturally occurs or is initially prepared from. Thus, for example, an isolated substance may be prepared by using a purification technique to enrich it from a source mixture. Enrichment can be measured on an absolute basis, such as weight per volume of solution, or it can be measured in relation to a second, potentially interfering substance present in the source mixture. Increasing enrichments of the embodiments of this invention are increasingly more preferred. Thus, for example, a 2-fold enrichment is preferred, 10-fold enrichment is more preferred, 100-fold enrichment is more preferred, 1000-fold enrichment is even more preferred.

An "individual" or "subject" treated in accordance with this invention refers to vertebrates, particularly members of a mammalian species, and includes but is not limited to domestic animals, sports animals, and primates, including humans.

"Treatment" of an individual or a cell is any type of intervention in an attempt to alter the natural course of the individual or cell at the time the treatment is initiated. For example, treatment of an individual may be undertaken to decrease or limit the pathology caused by any pathological condition, including (but not limited to) an inherited or induced genetic deficiency, infection by a viral, bacterial, or parasitic organism, a neoplastic or aplastic condition, or an immune system dysfunction such as autoimmunity or immunosuppression. Treatment includes (but is not limited to) administration of a composition, such as a pharmaceutical composition, and administration of compatible cells that have been treated with a composition. Treatment may be performed either prophylactically or therapeutically; that is, either prior or subsequent to the initiation of a pathologic event or contact with an etiologic agent.

The term "effective amount" refers to an amount of a substance sufficient to achieve the intended purpose. For example, an effective amount of an expression vector to increase sulfamidase activity is an amount sufficient to reduce glycosaminoglycan accumulation. A "therapeutically effective amount" of an expression vector to treat a disease or disorder is an amount of the expression vector sufficient to reduce or remove the symptoms of the disease or disorder. The effective amount of a given substance will vary with factors such as the nature of the substance, the route of administration, the size and species of the animal to receive the substance and the purpose of giving the substance. The effective amount in each individual case may be determined empirically by a skilled artisan according to established methods in the art.

The term "gene therapy" refers to the transfer of genetic material (e.g. DNA or RNA) of interest into a host to treat or prevent a genetic or acquired disease or condition. The genetic material of interest encodes a product (e.g. a protein polypeptide, peptide or functional RNA) whose production in vivo is desired. For example, the genetic material of interest can encode an enzyme, hormone, receptor, or polypeptide of therapeutic value.

DETAILED DESCRIPTION OF THE INVENTION

It is an object of this invention to provide methods for generating high titer preparations of recombinant viral vectors, in particular, recombinant adeno-associated viral vectors (rAAV) so that the methods can be effectively employed on a scale that is suitable for the practical application of gene therapy procedures.

As it is shown in the Examples accompanying the present invention, the inventors have found that, surprisingly, rAAV production can be significantly improved by performing repeated rounds of transfection, i.e. by re-transfections, of the cell culture with the plasmid vectors used for triple or double transfection.

Thus, in a first aspect, the invention refers to a method for the production of a recombinant viral vector said method comprising the steps of:
  a) co-transfecting a suitable cell culture with at least two plasmid vectors, said plasmid vectors comprising a heterologous nucleotide sequence and replication and packaging gene sequences;
  b) culturing said cells under conditions Rowing viral replication and packaging;
  c) recovering the viral vectors produced in step b) and retaining the cells in the cell culture under conditions allowing further division and growth;
  d) re-transfecting the cells according to step c) with the plasmid vectors according to step a); and
  e) repeating steps b) to c).

In a particular embodiment of the invention, said recombinant viral vector is selected from the group consisting of an adenovirus, adeno-associated virus (AAV), alphavirus, flavivirus, herpes simplex virus (HSV), measles virus, rhabdovirus, retrovirus, lentivirus, Newcastle disease virus (NDV), poxvirus, and picornavirus. In a particular embodiment, said viral vector is selected a retroviral vector, an adenoviral vector or an AAV vector.

In a preferred embodiment, said viral vector is an AAV vector.

AAV according to the present invention include any serotype of the AAV known serotypes. In general, the different serotypes of AAV have genomic sequences with a significant homology, providing an identical series of genetic functions, produce virions that are essentially equivalent in physical and functional terms, and replicate and assemble through practically identical mechanisms. In particular, the AAV of the present invention may belong to the serotype 1 of AAV (AAV1), AAV2, AAV3 (including types 3A and 3B), AAV4, AAV5, AAV6, AAV7, AAV8, AAV9, AAV10, AAV11, avian AAV, bovine AAV, canine AAV, equine AAV, ovine AAV, and any other AAV. Examples of the sequences of the genome of the different AAV serotypes may be found in the literature or in public databases such as GenBank. See GenBank accession numbers AF028704.1 (AAV6), NC006260 (AAV7), NC006261 (AAV8), and AX753250.1 (AAV9). In a preferred embodiment, the AAV vector of the invention is of a serotype selected from the group consisting of the AAV2, AAV5, AAV7, AAV8, AAV9, AAV10 and AAVrh10 serotypes. In a preferred embodiment, said AAV vector of the invention is of serotype 9.

In a particular embodiment, the invention refers to a method for the production of a recombinant AAV said method comprising the steps of:
a) co-transfecting a suitable cell culture with at least two plasmid vectors said vectors comprising a heterologous nucleotide sequence flanked by ITRs, AAV rep and AAV cap gene sequences, and adenovirus helper functions sequences;
b) culturing said cells under conditions allowing AAV replication and packaging;
c) recovering the AAVs produced in step b) and retaining the cells in the cell culture under conditions allowing further division and growth,
d) re-transfecting the cells according to step c) with the plasmid vectors according to step a), and
e) repeating steps b) to c).

As it is described in the art, genetic material can be introduced into cells using any of a variety of means to transform or transduce such cells. By way of illustration, such techniques include, for example, transfection with bacterial plasmids. Indeed, the plasmid vectors according to step a) of the method of the invention can be introduced into a cell using a variety of transfection techniques. Such transfection methods have been described in the art and include, for example, calcium phosphate co-precipitation, direct micro-injection into cultured cells, electroporation, liposome mediated gene transfer, lipid-mediated transfection or nucleic acid delivery using high-velocity microprojectiles. Other suitable transfection media include strontium phosphate, polycationic polymers, e.g., Superfect (QIAGEN™) liposomes, and cationic polymers such as polyethylenimine (PEI). In a preferred embodiment, the plasmid vectors according to the method of the invention are transfected using PEI. In this case, PEI/DNA complexes are formed by adding PE to plasmid DNA prior to its addition to the cell culture.

Any of these techniques can be used to introduce one or more, exogenous DNA moieties, such as vector constructs, into suitable host cells. Generally, the exogenous DNA must traverse the host cell plasma membrane in order to be exposed to the cell's transcription and replication machinery.

The resulting cell can be transiently transfected with the exogenous nucleic acid molecule, i.e., the exogenous DNA will not be integrated into the genome of a transfected cell, but rather will exist episomally. Alternatively, the resulting cell can be stably transfected, i.e., the nucleic acid molecule will become covalently linked with the host cell genome or will be maintained and replicated as an episomal unit which can be passed on to progeny cells (e.g., capable of extra-chromosomal replication at a sufficient rate).

According to the method of the invention, the plasmid vectors to be transfected comprise a heterologous nucleotide sequence flanked by the ITRs. AAV rep and AAV cap gene sequences, and adenovirus helper functions sequences.

The heterologous nucleotide sequence or polynucleotide is typically of interest because of a capacity to provide a function to a target cell in the context of gene therapy, such as up- or down-regulation of the expression of a certain phenotype. Such a heterologous polynucleotide or "transgene" will generally be of sufficient length to provide the desired function or encoding sequence.

Where transcription of the heterologous polynucleotide is desired in the intended target cell, it can be operably linked to its own or to a heterologous promoter, depending for example on the desired level and/or specificity of transcription within the target cell, as is known in the art. Various types of promoters and enhancers are suitable for use in this context. Constitutive promoters provide an ongoing level of gene transcription, and are preferred when it is desired that the therapeutic polynucleotide be expressed on an ongoing basis. Inducible promoters generally exhibit low activity in the absence of the inducer, and are up-regulated in the presence of the inducer. They may be preferred when expression is desired only at certain times or at certain locations, or when it is desirable to titrate the level of expression using an inducing agent. Promoters and enhancers may also be tissue-specific, that is, they exhibit their activity only in certain cell types, presumably due to gene regulatory elements found uniquely in those cells.

Illustrative examples of promoters are the SV40 late promoter from simian virus 40, the Baculovirus polyhedron enhancer/promoter element, Herpes Simplex Virus thymidine kinase (HSV tk), the immediate early promoter from cytomegalovirus (CMV), the CMV early enhancer/chicken β actin (CAG) promoter and various retroviral promoters including LTR elements. Inducible promoters include heavy metal ion inducible promoters (such as the mouse mammary tumor virus (mMTV) promoter or various growth hormone promoters), and the promoters from T7 phage which are active in the presence of T7 RNA polymerase. By way of illustration, examples of tissue-specific promoters include various surfactant proteins promoters (for expression in the lung), myosin promoters (for expression in muscle), and albumin promoters or human α1-antitrypsin hAAT (for expression in the liver). A large variety of other promoters are known and generally available in the art, and the sequences for many such promoters are available in sequence databases such as the GenBank database. In a preferred embodiment, the CAG promoter is used.

Where translation is also desired in the intended target cell, the heterologous polynucleotide will preferably also comprise control elements that facilitate translation (such as a ribosome binding site or "RBS" and/or a polyadenylation signal). Accordingly, the heterologous polynucleotide will generally comprise at least one coding region operatively linked to a suitable promoter, and may also comprise, for example, an operatively linked enhancer, ribosome binding site and/or poly-A signal. The heterologous polynucleotide may comprise one coding region, or more than one coding regions under the control of the same or different promoters. The entire unit, containing a combination of control elements and coding or non-coding region, is often referred to as an expression cassette. In a particular embodiment, the heterologous polynucleotide according to the method of the invention contains a poly-A signal.

The heterologous polynucleotide is integrated by recombinant techniques into or preferably in place of the AAV genomic coding region and is generally flanked on either side by AAV inverted terminal repeat (ITR) regions. Alternatively, vector constructs with only one ITR can be employed. In a particular embodiment, said heterologous nucleotide sequence is flanked by two ITRs.

Given the encapsidation size limit of the AAV particles, insertion of a large heterologous polynucleotide into the genome necessitates removal of a portion of the AAV sequence. Removal of one or more AAV genes is in any case desirable, to reduce the likelihood of generating replication-competent AAV ("RCA"). Accordingly, encoding or promoter sequences for rep, cap, or both, are preferably removed, since the functions provided by these genes can be provided in trans.

In one embodiment, the heterologous nucleotide sequence is flanked by AAV ITRs, and the AAV packaging genes to be provided in trans, are introduced into the host cell in separate vector plasmids.

The rep gene is expressed from two promoters, p5 and p19, and produces four proteins designated Rep78, Rep68, Rep52 and Rep40. Only Rep78 and Rep68 are required for AAV duplex DNA replication, but Rep52 and Rep40 appear to be needed for progeny, single-strand DNA accumulation. Rep68 and Rep78 bind specifically to the hairpin conformation of the AAV ITR and possess several enzyme activities required for resolving replication at the AAV termini. Rep78 and Rep68, also exhibit pleiotropic regulatory activities including positive and negative regulation of AAV genes and expression from some heterologous promoters, as well as inhibitory effects on cell growth.

The cap gene encodes capsid proteins VP1, VP2, and VP3, These proteins share a common overlapping sequence, but VP1 and VP2 contain additional amino terminal sequences transcribed from the p40 promoter by use of alternate initiation codons. All three proteins are required for effective capsid production.

Packaging of an AAV vector into viral particles still relies on the presence of a suitable helper virus for AAV or the provision of helper virus functions. According to the method of the present invention, helper virus function gene sequences are provided in plasmid vectors. The presence of significant quantities of infectious helper virus in a preparation of AAV vectors is problematic in that the preparation is intended for use in human administration.

In a particular embodiment of the method of the invention, transfection is performed using two plasmid vectors wherein one of said plasmid vectors comprises a heterologous nucleotide sequence flanked by ITRs and the second plasmid vector comprises the AAV rep and AAV cap gene sequences and adenovirus helper functions sequences. In a preferred embodiment, said second plasmid vector comprises from 5' to 3' an AAV rep coding region, an AAV cap coding region and a nucleotide sequence comprising an AAV p5 promoter region.

In a preferred embodiment of the method of the invention, transfection is performed using three plasmid vectors, i.e. the host cells are triple-transfected with at least one vector encoding a heterologous nucleotide sequence of interest, at least one vector encoding AAV rep and cap genes, and at least one vector encoding, adenoviral accessory functions.

Selection of suitably altered cells may be conducted by any technique in the art. For example, the polynucleotide sequences used to alter the cell may be introduced simultaneously with or operably linked to one or more detectable or selectable markers as is known in the art. By way of illustration, one can employ a drug resistance gene as a selectable marker. Drug resistant cells can then be picked and grown, and then tested for expression of the desired sequence—i.e., a packaging gene product, or a product of the heterologous polynucleotide, as appropriate. Testing for acquisition, localization and/or maintenance of an introduced polynucleotide can be performed using DNA hybridization-based techniques (such as Southern blotting and other procedures as known in the art). Testing for expression can be readily performed by Northern analysis of RNA extracted from the genetically altered cells, or by indirect immunofluorescence for the corresponding gene product.

According to step b) of the method of the invention, the transfected cells are thus cultured under conditions allowing viral vector replication and packaging. In a particular embodiment, the cells are cultured under conditions allowing rAAV replication and packaging.

Several criteria influence selection of cells for use in producing rAAV particles as described herein. The more preferred cells and cell lines are those that can be easily grown in culture so as to facilitate large-scale production of recombinant AAV vector preparations. Where large-scale production is desired, the choice of production method will also influence the selection of the host cell. For example, some production techniques and culture vessels or chambers are designed for growth of adherent or attached cells, whereas others are designed for growth of cells in suspension. In the latter case, the host cell would thus preferably be adapted or adaptable to growth in suspension. According to the present invention, large-scale production of rAAVs is desired.

A variety of cells lines are contemplated for use in the large-scale production of rAAV. Particularly suitable for cell culture of rAAV are Human Embryo Kidney (HEK) 293 cell lines, either adherent or selected for growth in suspension. Examples of other suitable cell lines to produce rAAV include: Vero cells, HeLa cells, and CHO cell lines. As used herein, the term "cell line" refers to a population of cells capable of continuous or prolonged growth and division in vitro. Often, cell lines are clonal populations derived from a single progenitor cell. It is known in the art that spontaneous or induced changes can occur in karyotype during storage or transfer of such clonal populations. Therefore, cells derived from the cell line referred to may not be precisely identical to the ancestral cells or cultures Nevertheless, the term "cell line" includes such variants.

Once a cell line is selected, the cell culture device of choice is seeded with cells at a density suitable to support cell culture. The density of cells used to seed a particular device will depend on the size of the device. A variety of volumes may be used to grow the cells in the culture device of choice. The volume of medium used will vary according to the size of the culture device used to grow the culture cells. Large-scale production methods such as suspension culture may be used. AAV particles are then collected, and isolated from the cells used to prepare them.

Cells are cultured under conditions that are permissive for the replication AAV and packaging of the rAAV vector. Culture time is preferably adjusted to correspond to peak production levels. Preferably, at least 100 viral particles are produced per cell: more preferably at least about 1000 per cell, still more preferably at least about 10,000 per cell. Preferably, at least $0.5 \times 10^6$, more preferably at least about $1 \times 10^6$, even more preferably at least about $2 \times 10^6$ RU/ml AAV vectors are produced per $2 \times 10^5$ cells during the culture period.

Various growth media may be used in the disclosed invention to achieve large-scale cell growth and AAV production. The selection of growth medium varies depending on the type of cells being cultured. In a particular embodiment, said cells are mammalian cells. In a preferred embodiment, said cell is Human Embryo Kidney (HEK) 293 cell lines. More preferably, said cells are cells suitable for being grown in suspension.

For the culture of adherent cells, roller bottles (cylindrical tissue culture flasks rotated at a given velocity) are used in order to provide the necessary surface for cell attachment.

Alternatively, micro-carriers are also a suitable system to support adherent cell cultures. For the culture of suspension cells, stirred tank bioreactors are the most indicated systems, since they enable to reach high cell density cultures that in turn can provide large amounts of rAAV after purification.

In a particular embodiment of the invention, a rocking-motion-type bioreactor is used. In another particular embodiment a stirred tank bioreactor could also be used. Once the cell culture in the reactor reaches a given point, transfection of cells is performed as mentioned above.

According to the method of the invention, step c) comprises recovering the AAVs produced in step b) and maintaining the cells in the cell culture under conditions allowing further division and growth. In a preferred embodiment of the method, step b) is performed culturing said cell in suspension in agitated liquid medium.

According to a particular embodiment of the method of the invention, in step b) the AAVs produced are secreted to the supernatant of the cell culture. Thus, according to step c) of the method of the invention, the rAAVs are harvested from the supernatant and the cells are kept in the cell culture for further division and growth. The spent media or supernatant is then collected together with the rAAVs so produced since, as it is shown in the Examples below, AAVs are secreted to the supernatant of the cell culture without the need of cell lysis.

In a particular embodiment, the cell media of the cell culture is exchanged before re-transfection is performed, i.e. before step d). In a particular embodiment, the cell media exchange is performed by centrifugation. In a preferred embodiment, media exchange is performed by perfusion. In a more preferred embodiment, continuous media exchange is performed by perfusion. More preferably, said culture medium is automatically exchanged by a perfusion system. By this system, the culture is replenished with fresh medium while cell-free supernatant is removed using a cell retention device. This process is preferably performed at a constant harvest flow rat. In this regard, in a preferred embodiment, new, fresh, culture media is added to the retained cells in order to allow them to further divide and grow. The constant addition of nutrients and removal of toxic metabolites allows perfusion cultures to reach and sustain high cell densities over many weeks.

The inventors have found that surprisingly, it is possible to re-transfect the retained cells in the cell culture with the plasmid vectors as described above for step a) so that the production of AAVs can be prolonged. In this sense, more rAAVs are produced using the cells retained in the cell culture device which are allowed to further divide and grow. Thus, the inventors have found that by performing repeated rounds of transfection, production of rAAVs can be extended over time using the same cell culture. Moreover, as it can be seen in the Examples accompanying the present invention, the inventors have found that by doing these medium exchanges, AAVs are secreted to the supernatant of the cell culture without the need of cell lysis and can be harvested every time the medium exchange is performed before each re-transfection round. Another advantage of the proposed methodology is that rAAVs are recovered from the supernatant, this being an advantage from the purification point of view as cells do not need to be lysed to harvest the AAVs and thus, less contamination with host cell DNA and host cell protein occurs.

Hence, the method of the invention comprises a step d) of re-transfecting the retained cells according to step c) with the plasmid vectors according to step a).

According to step d) of the method of the invention, re-transfection or repeated rounds of transfection are performed in the cell culture, as opposed to the conventional transient gene expression (TGE) approach which entails a single transfection round without medium exchange.

Moreover, the inventors have found that surprisingly said re-transfection and recovering steps can be repeated more than two times using the same cell culture, in a particular embodiment of the method of the invention, steps d), b) and c) are repeated at least one more time after recovering step c). In another particular embodiment steps d), b) and c) are repeated at least twice after recovering step c). In a more particular embodiment, steps d), b) and c) are repeated at least three times after recovering step c). In a preferred embodiment, steps d), b) and c) are repeated at least four times after recovering step c). In a more particular embodiment, steps d), b) and c) are repeated between one and three times after recovering step c). In a more particular embodiment, steps d), b) and c) are repeated between one and two times after recovering step c). In a preferred embodiment, the method of the invention includes one repetition of steps d), b) and c) after recovering step c). In a preferred embodiment of the method of the invention, steps d), b) and c) are repeated one more time after recovering step c).

As mentioned before, in a particular embodiment of the method of the invention, continuous media exchange is performed by perfusion. In a preferred embodiment, every time transfection is to be performed, perfusion stands. This allows plasmid vectors to enter the cell. In a more preferred embodiment, perfusion stands for a period of time of at least 1.5 hours, more preferably, of at least 2 hours, more preferably of at least 3 hours, even more preferably of at least 4 hours. In a preferred embodiment, there is a minimum interval of time between each re-transfection round. In a more preferred embodiment, said re-transfections are performed after an interval of time of at least 36 hours, more preferably, of at least 48 hours.

In another particular embodiment, said method comprises an additional step of lysing the cells in the supernatant after all rounds of re-transfection and recovering are finished.

There are several well-known techniques in the state of the art that can be used for cell disruption or cell lysis. Although freeze-thawing and/or sonication can be used to disrupt the cells, such techniques are not very suitable to large-scale preparations. Mechanical lysis techniques are thus preferable in those regards. Detergents and other chemical agents can also be employed to mediate or facilitate lysis. Treatment of lysates with nucleases (such as benzonase) has been found to be helpful for reducing viscosity and improving filterability. Clarification, e.g. by microfiltration to separate vector from at least some portion of the cellular debris, is also helpful for promoting recovery and purification. In a particular embodiment of the invention, said lysing step according to the method of the invention comprises using a nuclease, more preferably, said nuclease is benzonase.

In a particular embodiment of the method of the invention, the supernatant collected containing the rAAVs of the invention as described above is further processed so that the rAVVs are purified. In this regard, in another particular embodiment, the process is performed in a bioreactor coupled to a cell retention membrane, so that the cells are retained inside the reactor system while the AAVs are collected via the membrane, in a clean supernatant, free of cellular debris and therefore making purification much easier.

In order to be particularly useful for the production of AAV for gene therapy, it is most desirable for the techniques to be "scalable", i.e. applicable in conjunction with large-scale manufacturing devices and procedures.

By way of illustration, the AAVs can be loaded on a positively charged anion-exchange column, such as an N-charged amino or imino resin (e.g. POROS or any DEAE, TMAE, tertiary or quaternary amine, or PEI-based resin) or a negatively charged cation-exchange column (such as HS, SP, CM or any sulfo-, phospho- or carboxy-based cationic resin). The column can be washed with a buffer. The column can be eluted with a gradient of increasing NaCl concentration or a gradient of decreasing pH and fractions can be collected and assayed for the presence of AAV and/or contaminants.

Other procedures can be used in place of or, preferably, in addition to the above-described anion and cation exchange procedures, based on inter-molecular associations mediated by features other than charge as is known in the art. Such other procedures include intermolecular associations based on ligand-receptor pairs (such as antibody-antigen or lectin-carbohydrate interactions), as well as separations based on other attributes of the molecules, such as molecular sieving chromatography based on size and/or shape.

The pool of AAV-containing fractions eluted from a column as described above can be concentrated and purified by tangential flow filtration (TFF). The preparation is filtered through a membrane, and the product is retained. The retained material can be diafiltered using the membrane with successive washes of a suitable buffer. The final sample is highly enriched for the product and can be filtered and stored for use.

Transfection with the vector plasmids can occur on the day cell seeding is performed, or may be done on day one, day two, day three, day four, or day five post cell seeding depending on the cell seeding density.

In one embodiment of the invention, the host cells of choice are triple-transfected with at least one vector encoding a heterologous nucleotide sequence of interest, at least one vector encoding AAV rep and cap genes, and at least one vector encoding adenoviral accessory functions. In a particular embodiment, triple-transfection is performed using PEI transfection.

Packaging of plasmid backbone sequences (reverse packaging) during rAAV production by transient transfection is a common problem well known in the art. The term "reverse packaging" as used herein refers to the encapsidation of the backbone of the ITR containing plasmid instead of the heterologous sequence. Indeed, for AAV vectors, the predominant species of packaged DNA impurities are the plasmid sequences adjacent to the ITR flanking the expression cassette, likely generated by reverse packaging from the ITR. The presence of these particles in the rAAV stocks may represent a safety issue for clinical applications.

As shown in Example 1 below, the combination of optimized plasmids for the transfection, results in higher yield than production with the standard plasmids commonly used for AAV vector production and lower reverse packaging of bacterial sequences. In particular, the inventors have found that when cells are transfected with three plasmid vectors wherein a first plasmid vector i) comprises an heterologous nucleotide sequence flanked by ITRs and a stuffer DNA sequence located outside said ITRs, wherein said stuffer sequence has a length between 4400 Kb and 4800 Kb so that the plasmid backbone size is above 5 Kb; a second plasmid vector ii) comprising from 5' to 3' an AAV rep coding region, an AAV cap coding region and a nucleotide sequence comprising a AAV p5 promoter region, and a third plasmid vector iii) comprising adenovirus helper functions including VA-RNA, E2A y E4 sequences, wherein said plasmid does not contain E3, pTB(E2B), and Ad ITR, protease sequences, rAAV production is significantly increased. In this regard, according to the results shown below, AAV yield is augmented by three times when the combination of these three optimized plasmids is used instead of a combination of standard plasmids. Moreover, reverse packaging is also significantly reduced when compared with a triple transfection using standard plasmids well-known for the skilled person in the art, i.e. a non-oversized plasmid comprising the heterologous nucleotide sequence, a pRepCap vector, for example a pRep2Cap9 vector, and a plasmid containing adenoviral sequences required for AAV production (VA-RNA, E2A y E4). As mentioned before, the optimized helper plasmid used in the present invention contains the adenovirus helper functions including VA-RNA, E2A y E4 sequences required for AAV production. Said plasmid has been modified so that it does not contain certain sequences including E3, pTB(E2B), and Ad ITR sequences.

Figure 3:
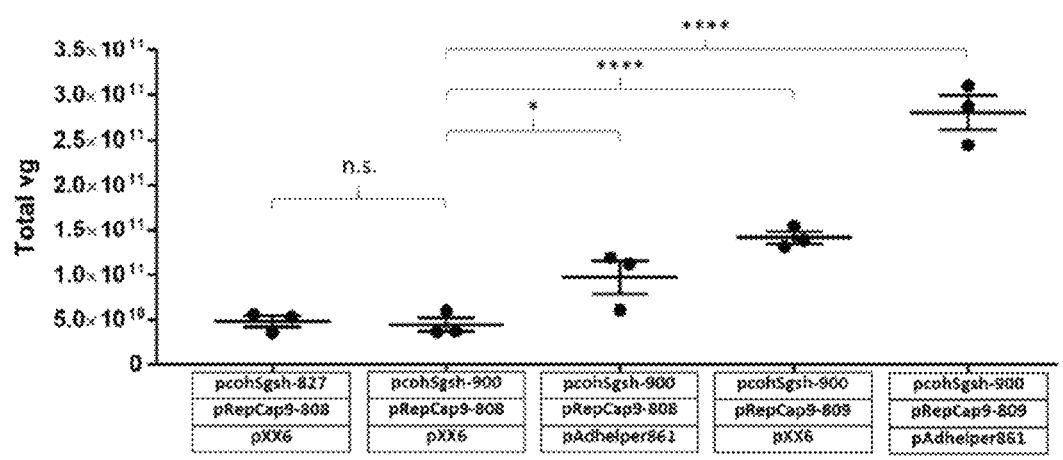

As it is clearly shown in FIG. 3, the use of an optimized plasmid containing an heterologous nucleotide sequence, wherein said plasmid is an oversized plasmid containing a stuffer DNA sequence, does not improve vector genome yield when used in combination with non-optimized plasmids i.e. with the standard vectors used for triple transfection. Thus, the use of an optimized oversized plasmid alone does not result in improvement of vector genome yield by triple transfection.

However, the combination of this optimized oversized plasmid with an optimized plasmid containing adenovirus helper functions (pAdhelper861) or an optimized plasmid containing AAV rep coding region and AAV cap coding region (pRepCap9-809) improved vector genome yield (see FIG. 3). Furthermore, when the three optimized vectors are combined, vector genome yield is greatly enhanced (see FIG. 3).

Figure 4:
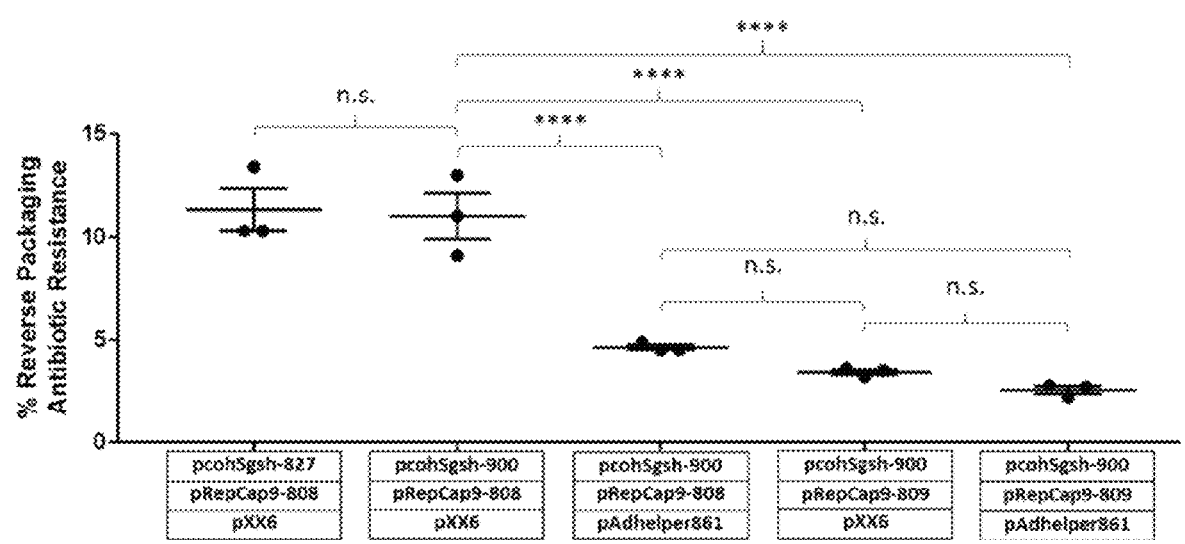
FIG. 4. Reverse packaging of bacterial sequences. Effect of the optimized oversized plasmid pcohSgsh-900 alone or in combination with the other optimized helper plasmids (pRepCap9-809 and pAdhelper861).
Figure 5:
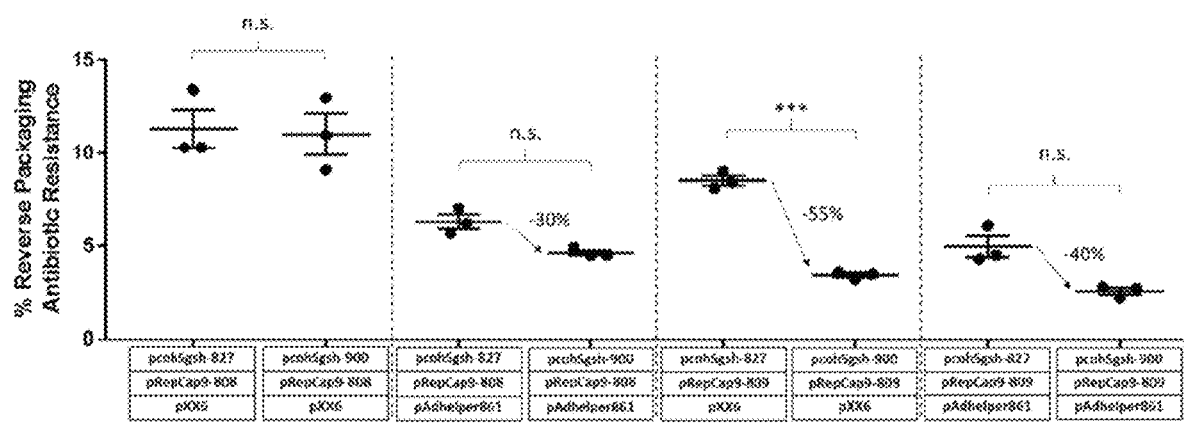
FIG. 5. Reverse packaging of bacterial sequences. Effect of the optimized oversized plasmid pcohSgsh-900 when combined with the other optimized helper plasmids (pRepCap9-809 and pAdhelper861), FIG. 6. Total vg recovered after transient transfection with pohIDS-874 plasmid. Cell lysis and total vg recovered in the culture supernatant after performing several re-transfection rounds. Time is represented in hours post transfection (hpt).
Figure 6:
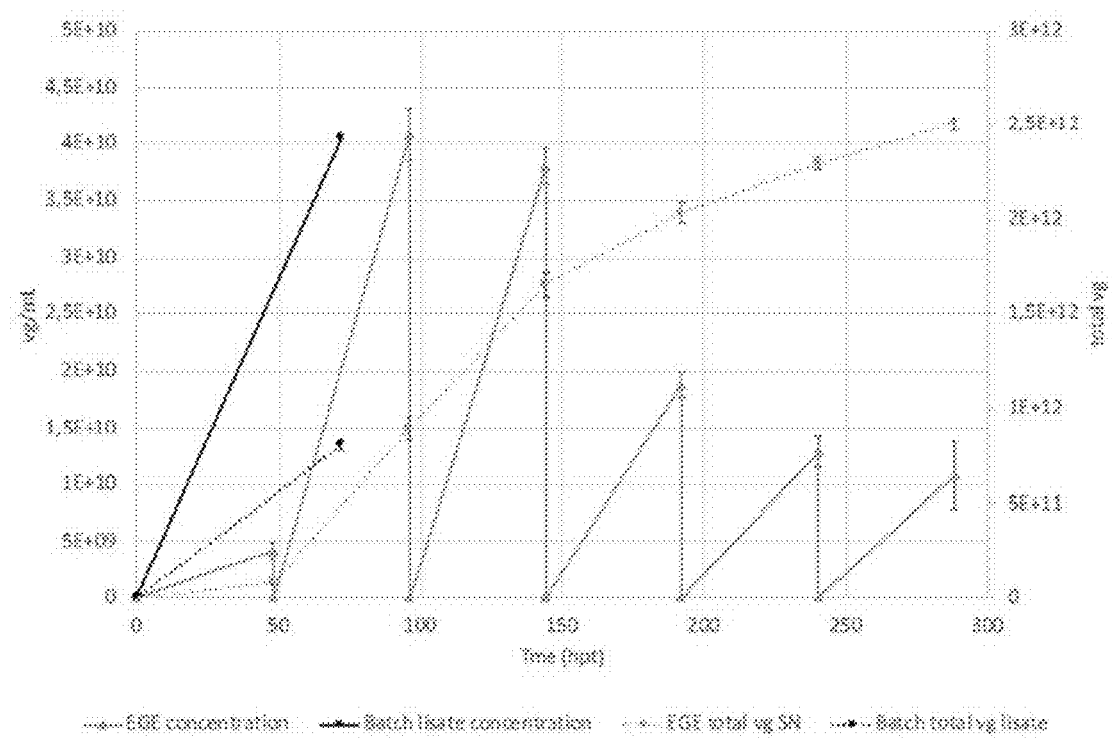
Figure 7:
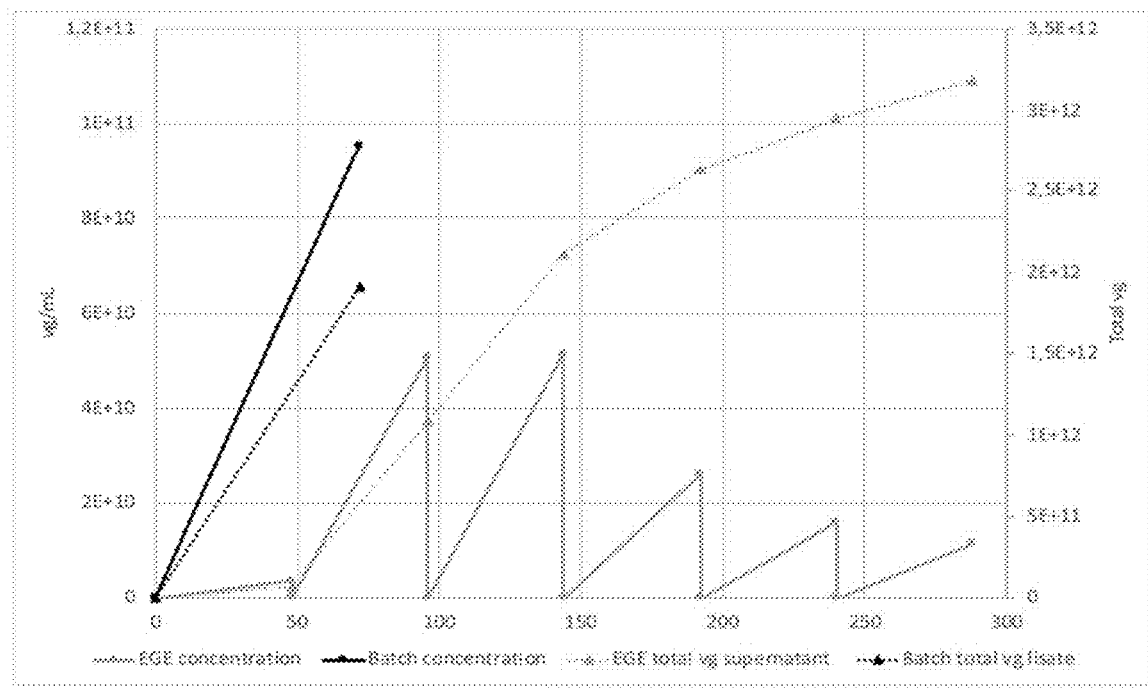
FIG. 7. Total vg recovered after transient transfection with pohSGSH-900 plasmid, Cell lysis and total vg recovered in the culture supernatant after performing several re-transfection rounds. Time is represented in hours post transfection (hpt).

Moreover, the inventors have surprisingly found a reduction of reverse packaging of bacterial sequences when co-transfection of the optimized oversized plasmid (pcohSgsh-900) with either one or both optimized helper plasmids, pRepCap9-809 and/or pAdhelper861 is performed (FIG. 4). In particular, the use of the triple combination of these optimized plasmids results in a greater reduction in reverse packaging (FIGS. 4 and 5). Indeed, the reduction in the percentage of bacterial sequences due to the use of optimized helper plasmids (pAdhelper861) and/or (pRepCap9-809) was more pronounced when the optimized plasmid containing an oversized backbone (pcohSgsh-900) was co-transfected (FIG. 5).

The term "oversized backbone" as used herein refers to a plasmid backbone with a size in base pairs above the limit of encapsidation of the AAV vectors (approx. 4700 bp).

In a preferred embodiment, said second plasmid vector used in the method of the invention comprises an AAV Rep2 and an AAV Cap9 coding regions. In a preferred embodiment, said plasmid vector is pRepCap-809 with accession number DSM 32 as set forth in SEQ ID NO: 5.

Thus, in a particular embodiment of the method of the invention, in step a) the following three-plasmid vectors are used:
  i) a first plasmid vector comprising a heterologous nucleotide sequence flanked by ITRs and a stuffer DNA sequence located outside said ITRs, wherein said stuffer sequence has a length between 4400 Kb and 4800 Kb so that the plasmid backbone size is above 5 Kb;

ii) a second plasmid vector comprising from 5' to 3' an AAV rep coding region, an AAV cap coding region and a nucleotide sequence comprising an AAV p5 promoter region; and iii) a third plasmid vector comprising adenovirus helper functions including VA-RNA. E2A y E4 sequences, wherein said plasmid does not contain E3, pTB(E2B), and Ad ITR protease sequences.

In a particular embodiment, the stuffer DNA sequence is located adjacent to one of the ITRs in the first plasmid vector composing the heterologous nucleotide sequence.

In another particular embodiment, the plasmid backbone size is between 7000 bp and 7500 bp. In a more particular embodiment, the plasmid backbone size is between 7000 bp and 7200 bp.

In a preferred embodiment, said first plasmid vector does not contain an F1Ori nucleotide sequence in the backbone sequence.

In a more preferred embodiment, said first plasmid vector is pcohSgsh-900 with accession number DSM 32967, as set forth in SEQ ID NO: 2.

According to another embodiment of the method of the invention, it is possible to re-transfect the remaining cells in the cell culture with two plasmid vectors so that the production of AAVs can be prolonged as explained above.

Thus, the invention also refers to a method according to the invention wherein in step a) the following two plasmid vectors are used:

i) a first plasmid vector comprising a heterologous nucleotide sequence flanked by ITRs and a stuffer DNA sequence located outside said ITRs, preferably, adjacent to one ITR, wherein said stuffer sequence has a length between 4400 Kb and 4800 Kb so that the plasmid backbone size is above 5 Kb, preferably between 7000 bp and 7500 bp, more preferably between 7000 bp and 7200 bp; and ii) a second plasmid vector comprising an AAV rep coding region, an AAV cap coding region, a nucleotide sequence comprising an AAV p5 promoter region, and adenovirus helper functions including VA-RNA, E2A and E4 sequences, wherein said plasmid does not contain E3, pTB(E2B), and Ad ITR Protease sequences.

In another particular embodiment, said second plasmid vector comprises from 5' to 3' the adenovirus helper functions including VA-RNA, E2A and E4 sequences, an AAV rep coding region, an AAV cap coding region, a nucleotide sequence comprising an AAV p5 promoter region.

In a particular embodiment, said first plasmid vector does not contain an F1Ori nucleotide sequence in the backbone sequence.

In another particular embodiment, said second plasmid vector comprises AAV Rep2 and AAV Cap9 coding regions.

As mentioned before, the combination of optimized plasmids for the transfection, results in higher yield than production with the standard plasmids commonly used for AAV vector production and lower reverse packaging of bacterial sequences.

In the Examples below it is shown that when production of rAAVs is performed using i) a plasmid vector comprising the heterologous nucleotide sequence flanked by ITRs; ii) a plasmid vector comprising from 5' to 3' an AAV rep coding region, an AAV cap coding region and a nucleotide sequence comprising a AAV p5 promoter region; and iii) a plasmid vector comprising adenovirus helper functions including VA-RNA, E2A y E4 sequences, wherein said plasmid does not contain E3, pTB(E2B), and Ad ITR protease sequences, reverse packaging is significantly reduced and moreover, productivity is increased, when compared with standard plasmids used for the production of AAVs by triple transfection.

Thus, in another aspect the invention refers to a method for the production of a recombinant AAV said method comprising the steps of:

a) co-transfecting a suitable cell with
i) a first plasmid vector comprising a heterologous nucleotide sequence flanked by ITRs;
ii) a second plasmid vector composing from 5' to 3' an AAV rep coding region, an AAV cap coding region and a nucleotide sequence comprising an AAV p5 promoter region: and
iii) a third plasmid vector comprising adenovirus helper functions including VA-RNA, E2A y E4 sequences, wherein said plasmid does not contain E3, pTB (E2B), and Ad 1TR protease sequences;

b) culturing said cell under conditions allowing AAV replication and packaging; and c) recovering the AAVs produced in step b).

In a preferred embodiment, said first plasmid vector i) is characterized in that the plasmid backbone size is above 5000 pb, preferably between 7000 bp and 7500 bp, more preferably, between 7000 bp and 7200 bp, and that it comprises a stuffer DNA sequence located outside said ITRs, preferably adjacent to one of the ITRs, and wherein said stuffer sequence has a length between 4400 pb and 4800. In a more preferred embodiment, said first plasmid vector i) does not contain an F1Ori nucleotide sequence in the backbone sequence. In a more preferred embodiment of the invention, said first plasmid is pcohSgsh-900 with accession number DSM 32967, as set forth in SEQ ID NO: 2.

In another preferred embodiment, said second plasmid vector ii) comprises AAV Rep2 and AAV Cap9 coding regions. In a preferred embodiment, said plasmid vector is pRepCap-809 with accession number DSM 32969 as set forth in SEQ ID NO: 5.

In another preferred embodiment, said third plasmid vector iii) is pAdHelper861 with accession number DSM 32965 as set forth in SEQ ID NO: 6.

As mentioned above, in another particular embodiment of the invention, step b) is performed culturing said cell in suspension in agitated liquid medium.

In another aspect, the invention also refers to a plasmid vector comprising:

a) a heterologous nucleotide sequence flanked by ITRs; and b) a stuffer DNA sequence located outside said ITRs and adjacent to one ITR, wherein said stuffer sequence has a length between 4400 Kb and 4800 Kb, more preferably, between 4500 Kb and 4700 Kb, even more preferably between 4600 Kb and 4700 Kb, so that the plasmid backbone size is above 5 Kb, preferably between 7000 bp and 7500 bp; more preferably, between 7000 bp and 7200 bp;

wherein said plasmid vector does not contain a F1Ori nucleotide sequence in the backbone sequence. #n a more preferred embodiment of the invention, said plasmid is pcohSgsh-900 with accession number DSM 32967, as set forth in SEQ ID NO: 2.

In another particular aspect, the invention refers to a helper plasmid vector containing the adenoviral sequences E2, E4 and VA-RNA wherein said plasmid vector does not contain E3, pTB(E2B), and Ad ITR Protease sequences, More particularly, this plasmid, contains a region of 731 bp that includes the VA genes, a 5346 bp region that includes the E2A gene and the E4 genes and their regulatory regions are included into a 3181 bp fragment. The plasmid backbone contains a high copy number bacterial origin of replication. In a more preferred embodiment, the invention refers to the plasmid vector of SEQ ID NO: 6 which corresponds to pAdHelper861 deposited under accession number DSM 32965.

Use of rAAV for Gene Therapy

The rAAV viral vectors of this invention can be used for administration to an individual for purposes of gene therapy. Suitable diseases for gene therapy include but are not limited to those induced by viral, bacterial, or parasitic infections, various malignancies and hyperproliferative conditions, autoimmune conditions, and congenital deficiencies. In a preferred embodiment, the rAAV vectors produced according to the method of the invention are used for the treatment of lysosomal storage diseases (LSDs). More preferably, said vectors are helpful for the treatment of mucopolysaccharidoses (MPS). In a preferred embodiment, said heterologous nucleotide sequence is a sequence that codifies for an enzyme useful for the treatment of MPS. In particular, said sequence is selected from the group consisting of human α-L-iduronidase, human heparan sulfamidase, human N-sulfoglucosamine sulfohydrolase, human N-acetylglucosaminidase, alpha, human heparan-o-glucosaminide, human N-acetyltransferase, human Iduronate 2-sulfatase (IDS), human N-acetylglucosamine 6-sulfatase, human galactose-6-sulfate sulfatase, human β-galactosidase, human N-acetylgalactosamine-4-sulfatase, β-glucuronidase, and human hyaluronidase.

Gene therapy can be conducted to enhance the level of expression of a particular protein either within or secreted by the cell. Vectors of this invention may be used to genetically alter cells either for gene marking, replacement of a missing or defective gene, or insertion of a therapeutic gene. Alternatively, a polynucleotide may be provided to the cell that decreases the level of expression. This may be used for the suppression of an undesirable phenotype, such as the product of a gene amplified or overexpressed during the course of a malignancy, or a gene introduced or overexpressed during the course of a microbial infection. Expression levels may be decreased by supplying a therapeutic polynucleotide comprising a sequence capable, for example, of forming a stable hybrid with either the target gene or RNA transcript (antisense therapy), capable of acting as a ribozyme to cleave the relevant mRNA or capable of acting as a decoy for a product of the target gene.

Pharmaceutical compositions can be supplied as liquid solutions or suspensions, as emulsions, or as solid forms suitable for dissolution or suspension in liquid prior to use. The carrier is, for instance, water, or a buffered saline solution, with or without a preservative.

The pharmaceutical compositions may be lyophilized for re-suspension at the time of administration or in solution. In a preferred embodiment, the pharmaceutical composition of the invention is a suspension for injection. The final product is then formulated in a suitable buffer, filled in vials and stored until use.

Although not required, pharmaceutical compositions may optionally be supplied in unit dosage form suitable for administration of a precise amount.

Having described the invention in general terms, it will be more easily understood by reference to the following examples which are presented as an illustration and are not intended to limit the present invention in any way.

EXAMPLES

The practice of the present invention will employ, unless otherwise indicated, conventional techniques of molecular biology, virology, animal cell culture and biochemistry which are within the skill of the art. Such techniques are explained fully in the literature.

Example 1

Triple Transfection Using Standard Plasmid Vectors vs Optimized Vectors 1.1. Plasmid Description Plasmid pcohSgsh-827 (SEQ ID NO: 1)

Plasmid containing a 1512 bp codon optimized cDNA that codifies for the human N-sulfoglucosamine sulfohydrolase under the control of the 1756 bp CAG promoter and a 519 bp fragment corresponding to the rabbit b-globin pA. These three elements are flanked by the AAV 2 ITR sequences. The plasmid backbone size is 3156 bp (standard backbone size) and comprises a 966 bp ampicillin resistance gene, a 514 bp bacteriophage origin of replication and a 589 bp high copy number bacterial origin of replication.

Plasmid pcohSgsh-900 (SEQ ID NO: 2)

Oversized plasmid containing a 1512 bp codon optimized cDNA that codifies for the human N-sulfoglucosamine sulfohydrolase under the control of the 1756 bp CAG promoter and a 519 bp fragment corresponding to the rabbit b-globin pA. These three elements are flanked by the AAV 2 ITR sequences. The plasmid backbone is 7073 bp, comprises the 1043 bp kanamycin resistance gene, a 589 bp high copy number bacterial origin of replication and additionally includes a 4657 bp random sequence.

Plasmid pohIDS-874 (SEQ ID NO: 3)

Oversized plasmid containing a 1653 bp codon optimized cDNA that codifies for the human Iduronate 2-sulfatase under the control of the 1756 bp CAG promoter and a 519 by fragment corresponding to the rabbit b-globin pA. These three elements are flanked by the AAV 2 ITR sequences. The plasmid backbone is 7073 bp and comprises the 1043 bp kanamycin resistance gene, a 589 bp high copy number bacterial origin of replication and additionally includes a 4657 bp random sequence.

Plasmid pRepCap9-808 (SEQ ID NO: 4)

Plasmid encoding the rep2 and the cap9 proteins with the P5 promoter in its original position. This plasmid includes a 1866 bp fragment corresponding to the AAV2 Rep gene followed by a sequence of 2211 bp encoding the AAV9 Cap gene. The 130 bp AAV2 P5 promoter is located on its original position upstream of the Rep gene. The plasmid backbone comprises the ampicillin resistance gene and a high copy number bacterial origin of replication.

Plasmid pRepCap9-809 (SEQ ID NO: 5)

Plasmid encoding the rep2 and the cap9 proteins with the P5 promoter after the Cap9 gene. This plasmid includes a 1866 bp fragment corresponding to the AAV2 Rep gene followed by a sequence of 2211 bp encoding the AAV9 Cap gene. A sequence of 130 bp corresponding to the AAV2 P5 promoter is located downstream of the Cap gene. The plasmid backbone comprises the kanamycin resistance gene and a high copy number bacterial origin of replication.

Plasmid pXX6

Plasmid containing the adenoviral sequences (E2, E4 and VA-RNA) which are required for the AAV production. The plasmid backbone comprises the ampicillin resistance gene and a high copy number bacterial origin of replication (Xiao et al. J Virol. 1998 March; 72(3): 2224-2232). Plasmid pXX6-80 derives from pXX6 where only the backbone was changed. pXX6-80 map and sequence are well described in the literature.

Plasmid pAdHelper861 (SEQ ID NO: 6)

Plasmid containing the adenoviral sequences (E2, E4 and VA-RNA) which are required for the AAV production, it contains a region of 731 bp that includes the VA genes, a 5346 bp region that includes the E2A gene and the E4 genes and their regulatory regions are included into a 3181 bp fragment. The plasmid backbone comprises the kanamycin resistance gene and a high copy number bacterial origin of replication.

1.2. AAV9-CAG-cohSgsh Vector Production by Triple Transfection

Materials and Methods

AAV9-CAG-cohSgsh vectors were produced by transient triple-transfection using PEI-MAX as transfection agent as previously described (Ayuso E, et at. Gene Ther, 2010 April; 17(4):503-10). Briefly, HEK293 adherent cells at confluency were transfected with equimolar quantities of three plasmids: pcohSgsh-827, pRepCap9-808 and pXX6 (standard plasmids) or pcohSgsh-900, pRepCap9-809 and pAdHelper861 (optimized plasmids). PEE-MAX was used at a PEI:DNA ratio of 2:1. Cells were harvested 72 hours post-transfection and lysed by three cycles of freeze and thaw to release rAAV vectors from inside the cells (see Example 2 below). Production of rAAV vectors using suspension HEK293 cells has also been described (Joshua C Grieger, et al. Mol Ther. 2016 February; 24(2):1287-297), Vector genomes were quantified by Taqman qPCR as previously described (Ayuso et al. cited supra) using primers and probe specific for the rabbit beta-globin polyA sequence present in the expression cassette. Also, reverse packaging was quantified by Taqman qPCR with primers and probe specific for the antibiotic resistant promoter sequence present in all the plasmid backbones used.

Statistical analyses were performed with GraphPad Prism 7.00.

TABLE 1

List of plasmids used for the triple-transfection.

| Name | Plasmid type |
| --- | --- |
| pcohSgsh-827 | Standard |
| pRepCap9-808 | Standard |
| pXX6 | Standard |
| pcohSgsh-900 | Optimized |
| pRepCap9-809 | Optimaed |
| pAdHelper861 | Optimized |

Results

Production of recombinant AAV9 vectors AAV9-CAG-cohSgsh by triple transfection using optimized plasmids, as described above, results in higher yield than production with the standard plasmids commonly used for AAV vector production (FIG. 1).

Figure 2:
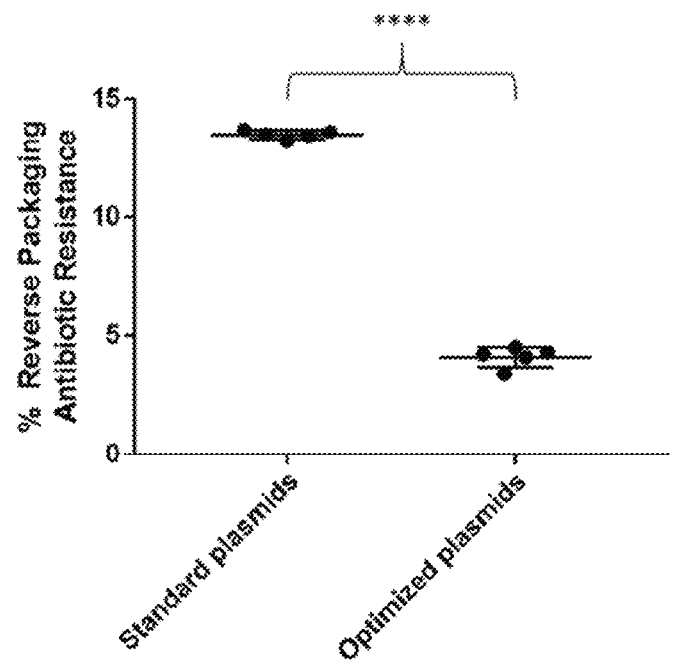
FIG. 2. Copies of bacterial sequence present in AAV9-CAG-cohSgsh produced by triple transfection with a set of standard plasmids or a set of optimized plasmids, FIG. 3. Effect of the optimized plasmid pcohSgsh-900 alone or in combination with the other optimized helper plasmids (pRepCap9-809 and pAdhelper861) on the AAV vector yield (total vg).

AAV9-CAG-cohSgsh vectors produced by triple transfection with the optimized plasmids result in lower reverse packaging of bacterial sequences than those obtained with the standard plasmids commonly used for AAV production (FIG. 2).

The use of an optimized plasmid containing an heterologous nucleotide sequence, wherein said plasmid is an oversized plasmid containing a stuffer DNA sequence (pcohSgsh-900), does not improve vector genome yield when used in triple transfection in combination with non-optimized plasmids. i.e. with the standard vectors used for triple transfections. Thus, the use of an optimized oversized plasmid alone does not result in improvement of vector genome yield by triple transfection (FIG. 3).

However, the combination of this optimized oversized plasmid with an optimized plasmid containing adenovirus helper functions (pAdhelper861) or an optimized plasmid containing AAV rep coding region and AAV cap coding region (pRepCap9-809) improved vector genome yield (see FIG. 3). Furthermore, when the three optimized vectors are combined, vector genome yield is greatly enhanced (see FIG. 3).

Moreover, the inventors have surprisingly found a reduction of reverse packaging of bacterial sequences when co-transfection of the optimized oversized plasmid (pcohSgsh-900) with either one or both optimized helper plasmids, pRepCap9-809 and/or pAdhelper861 is performed (FIG. 4). In particular, the use of the triple combination of these optimized plasmids results in a greater reduction in reverse packaging (FIGS. 4 and 5) Indeed, the reduction in the percentage of bacterial sequences due to the use of optimized helper plasmids (pAdhelper861) and/or (pRepCap9-809) was more pronounced when the optimized plasmid containing an oversized backbone (pcohSgsh-900) was co-transfected (FIG. 5).

Example 2

Triple Transfection and Extended Gene Expression (EGE)

2.1. Cell Line, Media, and Culture Conditions

The cell line used is a serum-free suspension-adapted HEK 293 cell line (HEK 293SF-3F6) provided by the Biotechnology Research Institute of National Research Council of Canada (Montreal, Canada). Cells are cultured in Freestyle F17 medium (Invitrogen, Carlsbad, CA) supplemented with, Glutamax 8 mM, 0.1% Pluronic1 (Invitrogen) and 0.05 ng/L IGF. Cells are routinely maintained in 125-mL disposable polycarbonate erlenmeyer flasks (Corning, Steuben, NY) in 20 mL of culture medium. Flasks are shaken at 130 rpm using an orbital shaker (Kuhner shakers, Switzerland) placed in an incubator maintained at 37° C. in a humidified atmosphere of 5% $CO_2$ in air. Cell count and viability are determined using Nucleocounter NC-3000 (Chemometec, Denmark).

2.2. Transient Transfection (TGE)

HEK 293 suspension cells are transiently transfected using PEIPro (Polysciences, Warrington, PA). HEK 293 cells are seeded at $0.5 \cdot 10^6$ cells/mL in 125-mL disposable flasks, grown to $2 \cdot 10^6$ cells/mL and transfected with 0.76 μg of pAdHelper861/mL of culture, 0.77 μg of pRepCap9-809/mL of culture and 0.38 μg of pohIDS-874/mL or 0.38 μg of pcohSgsh-900/mL of culture and a DNA to PEI mass ratio of 1.2. PEI/DNA complexes are formed by rapidly adding PEI to DNA, both diluted in fresh culture media to attain the same volume (complex mixture volume is 5% of the total volume of the culture to be transfected). The mixture is incubated for 15 min at room temperature to allow complex formation poor to its addition to the cell culture.

2.3. Extended Gene Expression Methodology for coh-IDS Gene

The Extended Gene Expression (EGE) production strategy consists in performing repeated rounds of transfection to achieve a sustained level of gene expression over time as opposed to the conventional TGE approach which entails a single transfection round. After the first transfection, using the same plasmids and conditions as described above in 2.2, retransfection rounds were performed every 48 hours using the same plasmid and PEI concentrations after a complete medium exchange performed by centrifugation (at 300×g during 5 minutes). By doing these medium exchanges, AAVs are secreted to the supernatant of the culture and can be harvested every time the medium exchange before each retransfection is performed.

The results show (See FIG. 3) a 3-fold increase in total vg harvested from the supernatant when EGE methodology is performed. Total vg recovered after Batch (single transfection) was 8E11 vg obtained after cell lysis. Total vg recovered after EGE strategy was 2.5E12 vg from the supernatant, this being an advantage from the purification point of view as cells do not need to be lysed to harvest the AAVs and thus less contamination with host cell DNA and host cell protein is expected.

2.4. Extended Gene Expression Methodology for coh-Sgsh Gene

The EGE methodology has also been tested for the gene coh-Sgsh as explained above in 2.3.

The results show (See FIG. 4) a 1.7-fold increase in total vg harvested from the supernatant when EGE methodology is performed. Total vg recovered after Batch (single transfection) was 1.9E12 vg obtained after cell lysis. Total vg recovered after EGE strategy was 3.18E12 vg from the supernatant. AAV production followed similar patterns that for phIDS (see 2.3 above) thus, supporting the general applicability of the EGE strategy.

The invention claimed is:

1. A method for the production of a recombinant Adeno-Associated Virus (AAV) vector, the method comprising the steps of:
   a) co-transfecting a suitable cell culture with three plasmid vectors:
   i) a first plasmid vector characterized in that the plasmid backbone size is above 5000 bp, and comprising a heterologous nucleotide sequence flanked by inverted terminal repeats (ITRs) and a stuffer DNA sequence located outside said ITRs, wherein said stuffer sequence has a length between 4400 bp and 4800 bp, wherein said plasmid vector does not contain an F1Ori nucleotide sequence in the backbone sequence, and wherein said plasmid vector is pcohSqsh-900 with accession number DSM 32967 having the sequence as set forth in SEQ ID NO: 2;
   ii) a second plasmid vector comprising from 5' to 3' an AAV rep coding region, an AAV cap coding region and a nucleotide sequence comprising a AAV p5 promoter region; and
   iii) a third plasmid vector comprising adenovirus helper functions including VA-RNA, E2A and E4 sequences, wherein said plasmid does not contain E3, pTB (E2B), and Ad ITR and protease sequences, and wherein said plasmid vector is pAdHelper-861 having accession number DSM 32965 having the sequence as set forth in SEQ ID NO: 6;
   b) culturing said cells under conditions allowing AAV replication and packaging;
   c) recovering recombinant AAVs produced in step b) and retaining the cells in the cell culture under conditions allowing further division and growth;
   d) re-transfecting the cells according to step c) with the plasmid vectors according to step a); and
   e) repeating steps b) to c).

2. The method of claim 1, wherein in step b) recombinant AAVs are secreted to the supernatant of the cell culture.

3. The method of claim 1, wherein the cell media of the cell culture is exchanged before step d).

4. The method of claim 3, wherein cell media exchange is performed by perfusion.

5. The method of claim 1, wherein steps d), b) and c) are repeated at least one more time after recovering step c).

6. The method of claim 1, wherein step b) is performed culturing said cell in suspension in agitated liquid medium.

7. A method for the production of a recombinant AAV vector the method comprising the steps of:
   a) co-transfecting a suitable cell with
   i) a first plasmid vector characterized in that the plasmid backbone size is above 5000 bp, and comprising a heterologous nucleotide sequence flanked by ITRs and a stuffer DNA sequence located outside said ITRs, wherein said stuffer sequence has a length between 4400 bp and 4800 bp, wherein said plasmid vector does not contain an F1Ori nucleotide sequence in the backbone sequence, and wherein said plasmid vector is pcohSgsh-900 with accession number DSM 32967 having the sequence as set forth in SEQ ID NO: 2;
   ii) a second plasmid vector comprising from 5' to 3' an AAV rep coding region, an AAV cap coding region and a nucleotide sequence comprising an AAV p5 promoter region; and
   iii) a third plasmid vector comprising adenovirus helper functions including VA-RNA, E2A and E4 sequences, wherein said plasmid does not contain E3, pTB (E2B), and Ad ITR and protease sequences, and wherein said plasmid vector is pAdHelper-861 having accession number DSM 32965 having the sequence as set forth in SEQ ID NO: 6;
   b) culturing said cell under conditions allowing AAV replication and packaging; and
   c) recovering recombinant AAVs produced in step b).

8. The method of claim 7, wherein said second plasmid vector (ii) comprises AAV Rep2 and AAV Cap9 coding regions.

9. A plasmid vector comprising:
   a) a heterologous nucleotide sequence flanked by inverted terminal repeats (ITRs); and b) a stuffer DNA sequence located outside said ITRs and adjacent to one ITR, wherein said stuffer sequence has a length between 4400 bp and 4800 bp so that the plasmid backbone size is above 5 Kb;

wherein said plasmid vector does not contain an F1Ori nucleotide sequence in the backbone sequence, and wherein said plasmid vector is pcohSgsh-900 with accession number DSM 32967 having the sequence as set forth in SEQ ID NO: 2.

10. A plasmid vector comprising adenovirus helper function sequences selected from the group consisting of VA-RNA, E2A and E4 sequences, wherein said plasmid does not contain E3, pTB (E2B), and Ad ITR and protease sequences, and wherein said plasmid vector is pAdHelper-861 having accession number DSM 32965 and having the sequence as set forth in SEQ ID NO: 6.

* * * * *

SEQUENCE LISTING

```
<160> NUMBER OF SEQ ID NOS: 6

<210> SEQ ID NO 1
<211> LENGTH: 7771
<212> TYPE: DNA
<213> ORGANISM: Artificial Sequence
<220> FEATURE:
<223> OTHER INFORMATION: Plasmid pcohSgsh-827

<400> SEQUENCE: 1
gctgcgcgct cgctcgctca ctgaggccgc ccgggcaaag cccgggcgtc gggcgacctt      60
tggtcgcccg gcctcagtga gcgagcgagc gcgcagagag ggagtggcca actccatcac     120 tagggggttcc ttgtagttaa tgattaaccc gccatgctac ttatctactc gacattgatt    180
attgactagt tattaatagt aatcaattac ggggtcatta gttcatagcc catatatgga     240
gttccgcgtt acataactta cggtaaatgg cccgcctggc tgaccgccca acgaccccg      300 cccattgacg tcaataatga cgtatgttcc catagtaacg ccaatagggg ctttccattg     360
acgtcaatgg gtggagtatt tacggtaaac tgcccacttg gcagtacatc aagtgtatca     420
tatgccaagt acgccccta ttgacgtcaa tgacggtaaa tggcccgcct ggcattatgc      480
ccagtacatg accttatggg actttcctac ttggcagtac atctacgtat tagtcatcgc     540
tattaccatg gtcgaggtga gccccacgtt ctgcttcact ctccccatct ccccccctc      600 cccaccccca attttgtatt tatttatttt ttaattattt tgtgcagcga tgggggcggg     660 ggggggggg gggcgcgcgc caggcggggc ggggcgggc gaggggcggg gcggggcgag       720
gcggagaggt gcggcggcag ccaatcagag cggcgcgctc cgaaagtttc cttttatggc     780
gaggcggcgg cggcggcggc cctataaaaa gcgaagcgcg cggcgggcgg gagtcgctgc     840
gcgctgcctt cgccccgtgc cccgctccgc cgccgcctcg cgccgcccgc cccggctctg     900
actgaccgcg ttactcccac aggtgagcgg gcgggacggc ccttctcctc cgggctgtaa     960
ttagcgcttg gtttaatgac ggcttgtttc ttttctgtgg ctgcgtgaaa gccttgaggg    1020
gctccgggag ggccctttgt gcggggggag cggctcgggg ggtgcgtgcg tgtgtgtgtg    1080
cgtggggagc gccgcgtgcg gctccgcgct gcccggcggc tgtgagcgct gcgggcgcgg    1140
cgcggggctt tgtgcgctcc gcagtgtgcg cgaggggagc gcggccgggg gcggtgcccc    1200
gcggtgcggg ggggctgcg aggggaacaa aggctgcgtg cggggtgtgt gcgtgggggg    1260
gtgagcaggg ggtgtgggcg cgtcggtcgg gctgcaaccc cccctgcacc cccctccccg    1320
agttgctgag cacggcccgg cttcgggtgc ggggctccgt acggggcgtg gcgcggggct    1380
cgccgtgccg ggcgggggt ggcggcaggt ggggtgccg ggcggggcgg ggccgcctcg     1440
ggccggggag ggctcggggg aggggcgcgg cggcccccgg agcgccggcg gctgtcgagg    1500
cgcggcgagc cgcagccatt gccttttatg gtaatcgtgc gagagggcgc agggacttcc    1560
tttgtcccaa atctgtgcgg agccgaaatc tgggaggcgc cgccgcaccc cctctagcgg    1620
gcgcggggcg aagcggtgcg gcgccggcag gaaggaaatg ggcggggagg gccttcgtgc    1680
```

```
gtcgccgcgc cgccgtcccc ttctccctct ccagcctcgg ggctgtccgc ggggggacgg      1740
ctgccttcgg gggggacggg gcagggcggg gttcggcttc tggcgtgtga ccggcggctc      1800
tagagcctct gctaaccatg ttcatgcctt cttcttttc ctacagctcc tgggcaacgt      1860
gctggttatt gtgctgtctc atcattttgg caaagaattg attaattcga gcgaacgcgt      1920
gccaccatga gctgccctgt gcccgcctgt tgtgccctgc tgctggtgct gggactgtgc      1980
agagccagac cccggaacgc tctgctgctg ctggccgacg atggcggatt tgagagcggc      2040
gcctacaaca cagcgccat tgccaccct catctggacg ccctggccag aagaagcctg      2100
ctgttccgga acgccttcac cagcgtgtcc agctgcagcc ctagcagagc ttccctgctg      2160
acaggcctgc cccagcatca gaatggcatg tacggcctgc accaggatgt gcatcacttc      2220
aacagcttcg acaaagtgcg gagcctgcca ctgctcctgt cacaggctgg cgtgagaacc      2280
ggcatcatcg gcaagaaaca cgtgggcccc gagacagtgt accccttcga cttcgcctac      2340
accgaagaga acggcagcgt gctgcaggtc ggccggaaca tcacccggat caagctgctc      2400
gtgcggaagt ttctccagac ccaggacgac cggcccttct tcctgtacgt ggccttccac      2460
gaccctcaca gatgcggcca cagccagccc cagtacggca ccttctgcga aagttcggc       2520 aacggcgaga gcggcatggg cagaatcccc gactggaccc ccaggcata cgaccctctg       2580 gacgtgctgg tgccctactt cgtgcccaac acccctgccg ccagagctga tctggccgcc      2640
cagtacacca ccgtgggcag aatggatcag ggcgtgggcc tggtgctgca ggaactgagg      2700
gacgctggcg tgctgaacga caccctggtc atcttcacct ccgacaacgg catcccattc      2760
cccagcggcc ggaccaatct gtactggccc ggcacagccg aacctctgct ggtgtccagc      2820
cccgagcacc ctaagagatg gggccaggtg tccgaggcct acgtgtccct gctggacctg      2880 accccccacca tcctggactg gttcagcatc ccctacccca gctacgccat ctttggaagc      2940
aagaccatcc acctgaccgg cagatctctg ctgcctgccc tggaagctga gcctctgtgg      3000
gccaccgtgt tcggcagcca gagccaccac gaagtgacca tgagctaccc catgcggagc      3060
gtgcagcacc ggcacttccg gctggtgcac aacctgaact tcaagatgcc cttcccaatc      3120
gaccaggact tttacgtgtc ccccaccttc caggacctgc tgaacagaac cacagccggc      3180
cagcccaccg gctggtacaa ggacctgcgg cactactact accgggccag atgggagctg      3240
tacgacagaa gccgggaccc ccacgagaca cagaacctgg ccaccgaccc cagattcgcc      3300
cagctcctgg aaatgctgcg ggaccagctg gccaagtggc agtgggagac acacgaccct      3360
tgggtctgcg ctccgacgg cgtgctgaa gagaagctgt cccccagtg ccagccactg      3420 cacaacgagc tgtgatgaga attcgagctc ggtacccggg aatcaattca ctcctcaggt      3480
gcaggctgcc tatcagaagg tggtggctgg tgtggccaat gccctggctc acaaatacca      3540
ctgagatctt tttccctctg ccaaaaatta tggggacatc atgaagcccc ttgagcatct      3600
gacttctggc taataaagga aatttatttt cattgcaata gtgtgttgga attttttgtg      3660
tctctcactc ggaaggacat atgggaggc aaatcattta aaacatcaga atgagtattt      3720
ggtttagagt ttggcaacat atgcccatat gctggctgcc atgaacaaag gttggctata      3780
aagaggtcat cagtatatga aacagccccc tgctgtccat tccttattcc atagaaaagc      3840
cttgacttga ggttagattt tttttatat ttgttttgtg ttatttttt ctttaacatc      3900 cctaaaattt tccttacatg ttttactagc cagattttc ctcctctcct gactactccc      3960
agtcatagct gtccctcttc tcttatggag atccctcgac ctgcagccca agctgtgata      4020
aagtagcatg gcgggttaat cattaactac aaggaacccc tagtgatgga gttggccact      4080
```

```
ccctctctgc gcgctcgctc gctcactgag gccgggcgac caaaggtcgc ccgacgcccg    4140
ggctttgccc gggcggcctc agtgagcgag cgagcgcgca gctgcattaa tgaatcggcc    4200
aacgcgcggg gagaggcggt ttgcgtattg ggcgctcttc cgcttcctcg ctcactgact    4260
cgctgcgctc ggtcgttcgg ctgcggcgag cggtatcagc tcactcaaag gcggtaatac    4320
ggttatccac agaatcaggg gataacgcag gaaagaacat gtgagcaaaa ggccagcaaa    4380
aggccaggaa ccgtaaaaag gccgcgttgc tggcgttttt ccataggctc cgcccccctg    4440
acgagcatca aaaatcgacg ctcaagtc agaggtggcg aaacccgaca ggactataaa      4500
gataccaggc gtttccccct ggaagctccc tcgtgcgctc tcctgttccg accctgccgc    4560
ttaccggata cctgtccgcc tttctccctt cgggaagcgt ggcgctttct catagctcac    4620
gctgtaggta tctcagttcg gtgtaggtcg ttcgctccaa gctgggctgt gtgcacgaac    4680
cccccgttca gcccgaccgc tgcgccttat ccggtaacta tcgtcttgag tccaacccgg    4740
taagacacga cttatcgcca ctggcagcag ccactggtaa caggattagc agagcgaggt    4800
atgtaggcgg tgctacagag ttcttgaagt ggtggcctaa ctacggctac actagaagaa    4860
cagtatttgg tatctgcgct ctgctgaagc cagttacctt cggaaaaaga gttggtagct    4920
cttgatccgg caaacaaacc accgctggta gcggtggttt ttttgtttgc aagcagcaga    4980
ttacgcgcag aaaaaagga tctcaagaag atcctttgat cttttctacg ggtctgacg      5040 ctcagtggaa cgaaaactca cgttaaggga ttttggtcat gagattatca aaaaggatct    5100
tcacctagat ccttttaaat taaaaatgaa gttttaaatc aatctaaagt atatatgagt    5160
aaacttggtc tgacagttac caatgcttaa tcagtgaggc acctatctca gcgatctgtc    5220
tatttcgttc atccatagtt gcctgactcc ccgtcgtgta gataactacg atacgggagg    5280
gcttaccatc tggccccagt gctgcaatga taccgcgaga cccacgctca ccggctccag    5340
atttatcagc aataaaccag ccagccgaa gggccgagcg cagaagtggt cctgcaactt     5400
tatccgcctc catccagtct attaattgtt gccgggaagc tagagtaagt agttcgccag    5460
ttaatagttt gcgcaacgtt gttgccattg ctacaggcat cgtggtgtca cgctcgtcgt    5520
ttggtatggc ttcattcagc tccggttccc aacgatcaag gcgagttaca tgatccccca    5580
tgttgtgcaa aaaagcggtt agctccttcg gtcctccgat cgttgtcaga agtaagttgg    5640
ccgcagtgtt atcactcatg gttatggcag cactgcataa ttctcttact gtcatgccat    5700
ccgtaagatg cttttctgtg actggtgagt actcaaccaa gtcattctga atagtgta     5760 tgcggcgacc gagttgctct tgcccggcgt caatacggga taataccgcg ccacatagca    5820
gaactttaaa agtgctcatc attggaaaac gttcttcggg gcgaaaactc tcaaggatct    5880
taccgctgtt gagatccagt tcgatgtaac ccactcgtgc acccaactga tcttcagcat    5940
cttttacttt caccagcgtt tctgggtgag caaaaacagg aaggcaaaat gccgcaaaaa    6000
agggaataag ggcgacacgg aaatgttgaa tactcatact cttcctttt caatattatt     6060 gaagcattta tcagggttat tgtctcatga gcggatacat atttgaatgt atttagaaaa    6120
ataaacaaat aggggttccg cgcacatttc cccgaaaagt gccacctgac gtctaagaaa    6180
ccattattat catgacatta acctataaaa ataggcgtat cacgaggccc tttcgtctcg    6240
cgcgtttcgg tgatgacggt gaaaacctct gacacatgca gctcccggag acggtcacag    6300
cttgtctgta agcggatgcc gggagcagac aagcccgtca gggcgcgtca gcgggtgttg    6360
gcgggtgtcg ggctggctt aactatgcgg catcagagca gattgtactg agagtgcacc     6420
```

```
atatgcggtg tgaaataccg cacagatgcg taaggagaaa ataccgcatc aggcgattcc      6480
aacatccaat aaatcataca ggcaaggcaa agaattagca aaattaagca ataaagcctc      6540
agagcataaa gctaaatcgg ttgtaccaaa acattatga ccctgtaata cttttgcggg       6600
agaagccttt atttcaacgc aaggataaaa attttagaa ccctcatata ttttaaatgc       6660
aatgcctgag taatgtgtag gtaaagattc aaacgggtga gaaaggccgg agacagtcaa     6720
atcaccatca atatgatatt caaccgttct agctgataaa ttcatgccgg agagggtagc     6780 tattttgag aggtctctac aaaggctatc aggtcattgc ctgagagtct ggagcaaaca       6840
agagaatcga tgaacggtaa tcgtaaaact agcatgtcaa tcatatgtac cccggttgat     6900
aatcagaaaa gccccaaaaa caggaagatt gtataagcaa atatttaaat tgtaagcgtt    6960 aatatttgt taaattcgc gttaaatttt tgttaaatca gctcattttt taaccaatag         7020
gccgaaatcg gcaaatccc ttataaatca aagaataga ccgagatagg gttgagtgtt        7080
gttccagttt ggaacaagag tccactatta agaacgtgg actccaacgt caaagggcga      7140
aaaaccgtct atcagggcga tggcccacta cgtgaaccat caccctaatc aagttttttg    7200
gggtcgaggt gccgtaaagc actaaatcgg aaccctaaag ggagccccg atttagagct     7260 tgacggggaa agccggcgaa cgtggcgaga aggaaggga agaaagcgaa aggagcgggc   7320
gctagggcgc tggcaagtgt agcggtcacg ctgcgcgtaa ccaccacacc cgccgcgctt    7380
aatgcgccgc tacagggcgc gtactatggt tgctttgacg agcacgtata acgtgctttc    7440
ctcgttagaa tcagagcggg agctaaacag gaggccgatt aaagggattt tagacaggaa   7500
cggtacgcca gaatcctgag aagtgttttt ataatcagtg aggccaccga gtaaaagagt   7560
ctgtccatca cgcaaattaa ccgttgtcgc aatacttctt tgattagtaa taacatcact    7620
tgcctgagta gaagaactca aactatcggc cttgctggta atatccagaa caatattacc    7680
gccagccatt gcaacggaat cgccattcgc cattcaggct gcgcaactgt tgggaagggc   7740
gatcggtgcg ggcctcttcg ctattacgcc a                                   7771

<210> SEQ ID NO 2
<211> LENGTH: 11255
<212> TYPE: DNA
<213> ORGANISM: Artificial Sequence
<220> FEATURE:
<223> OTHER INFORMATION: Plasmid pcohSgsh-900

<400> SEQUENCE: 2
attacgccag ctgcgcgctc gctcgctcac tgaggccgcc cgggcaaagc ccggcgtcg        60 ggcgaccttt ggtcgcccgg cctcagtgag cgagcgagcg cgcagagagg gagtggccaa    120
ctccatcact agggggttcct tgtagttaat gattaacccg ccatgctact tatctactcg    180
acattgatta ttgactagtt attaatagta atcaattacg gggtcattag ttcatagccc    240
atatatggag ttccgcgtta cataacttac ggtaaatggc ccgcctggct gaccgcccaa    300
cgacccccgc ccattgacgt caataatgac gtatgttccc atagtaacgc caatagggac    360
tttccattga cgtcaatggg tggagtattt acggtaaact gcccacttgg cagtacatca    420
agtgtatcat atgccaagta cgccccctat tgacgtcaat gacggtaaat ggcccgcctg    480
gcattatgcc cagtacatga ccttatggga ctttcctact tggcagtaca tctacgtatt    540
agtcatcgct attaccatgg tcgaggtgag ccccacgttc tgcttcactc tccccatctc     600 cccccctcc ccacccccaa ttttgtattt atttattttt taattatttt gtgcagcgat       660 ggggcgggg gggggggggg ggcgcgcgcc aggcggggcg gggcggggcg aggggcgggg      720
```

```
cggggcgagg cggagaggtg cggcggcagc caatcagagc ggcgcgctcc gaaagtttcc    780 tttatggcg aggcggcggc ggcggcggcc ctataaaaag cgaagcgcgc ggcgggcggg     840
agtcgctgcg cgctgccttc gccccgtgcc ccgctccgcc gccgcctcgc gccgcccgcc    900
ccggctctga ctgaccgcgt tactcccaca ggtgagcggg cggacgcc cttctcctcc     960 gggctgtaat tagcgcttgg tttaatgacg gcttgtttct tttctgtggc tgcgtgaaag  1020
ccttgagggg ctccgggagg gccctttgtg cgggggagc ggctcggggg gtgcgtgcgt  1080
gtgtgtgtgc gtggggagcg ccgcgtgcgg ctccgcgctg cccggcggct gtgagcgctg  1140
cgggcgcggc gcgggctttt gtgcgctccg cagtgtgcgc gaggggagcg cggccggggg  1200
cggtgccccg cggtgcgggg ggggctgcga ggggaacaaa ggctgcgtgc ggggtgtgtg  1260 cgtgggggg tgagcagggg gtgtgggcgc gtcggtcggg ctgcaacccc ccctgcaccc  1320
ccctccccga gttgctgagc acggcccggc ttcgggtgcg gggctccgta cggggcgtgg  1380
cgcggggctc gccgtgccgg gcggggggtg cggcaggtg ggggtgccgg gcggggcggg  1440
gccgcctcgg gccggggagg gctcgggga ggggcgcggc ggcccccgga gcgccggcgg  1500
ctgtcgaggc gcggcgagcc gcagccattg ccttttatgg taatcgtgcg agagggcgca  1560
gggacttcct ttgtcccaaa tctgtgcgga gccgaaatct gggaggcgcc gccgcacccc  1620
ctctagcggg cgcggggcga agcggtgcgg cgccggcagg aaggaaatgg gcggggaggg  1680
ccttcgtgcg tcgccgcgcc gccgtcccct tctccctctc cagcctcggg gctgtccgcg  1740
gggggacggc tgccttcggg ggggacgggg cagggcgggg ttcggcttct ggcgtgtgac  1800
cggcggctct agagcctctg ctaaccatgt tcatgccttc ttcttttttcc tacagctcct  1860 gggcaacgtg ctggttattg tgctgtctca tcattttggc aaagaattga ttaattcgag  1920
cgaacgcgtg ccaccatgag ctgccctgtg cccgcctgtt gtgccctgct gctggtgctg  1980
ggactgtgca gagccagacc ccggaacgct ctgctgctgc tggccgacga tggcggatt   2040 gagagcggcg cctacaacaa cagcgccatt gccacccctc atctggacgc cctggccaga  2100
agaagcctgc tgttccggaa cgccttcacc agcgtgtcca gctgcagccc tagcagagct  2160
tccctgctga caggcctgcc ccagcatcag aatggcatgt acggcctgca ccaggatgtg  2220
catcacttca acagcttcga caaagtgcgg agcctgccac tgctcctgtc acaggctggc  2280
gtgagaaccg gcatcatcgg caagaaacac gtgggcccg agacagtgta ccccttcgac  2340
ttcgcctaca ccgaagagaa cggcagcgtg ctgcaggtcg gccggaacat cacccggatc  2400
aagctgctcg tgcggaagtt tctccagacc caggacgacc ggccccttctt cctgtacgtg  2460 gccttccacg accctcacag atgcggccac agccagcccc agtacggcac cttctgcgag  2520
aagttcggca acgcgagag cggcatgggc agaatccccg actggacccc ccaggcatac  2580
gaccctctgg acgtgctggt gccctacttc gtgcccaaca ccctgccgc cagagctgat  2640 ctggccgccc agtacaccac cgtgggcaga atggatcagg gcgtgggcct ggtgctgcag  2700
gaactgaggg acgctggcgt gctgaacgac accctggtca tcttcacctc cgacaacggc  2760
atcccattcc ccagcggccg gaccaatctg tactggcccg gcacagccga acctctgctg  2820
gtgtccagcc ccgagcaccc taagagatgg ggccaggtgt ccgaggccta cgtgtccctg  2880 ctggaccctga ccccaccat cctggactgg ttcagcatcc cctaccccag ctacgccatc  2940
tttggaagca agaccatcca cctgaccggc agatctctgc tgcctgccct ggaagctgag  3000
cctctgtggg ccaccgtgtt cggcagccag agccaccacg aagtgaccat gagctacccc  3060
```

```
atgcggagcg tgcagcaccg gcacttccgg ctggtgcaca acctgaactt caagatgccc       3120
ttcccaatcg accaggactt ttacgtgtcc cccaccttcc aggacctgct gaacagaacc       3180
acagccggcc agcccaccgg ctggtacaag gacctgcggc actactacta ccgggccaga       3240
tgggagctgt acgacagaag ccgggacccc cacgagacac agaacctggc caccgacccc       3300
agattcgccc agctcctgga aatgctgcgg gaccagctgg ccaagtggca gtgggagaca       3360
cacgaccctt gggtctgcgc tcccgacggc gtgctggaag agaagctgtc cccccagtgc       3420
cagccactgc acaacgagct gtgatgagaa ttcgagctcg gtacccggga atcaattcac       3480
tcctcaggtg caggctgcct atcagaaggt ggtggctggt gtggccaatg ccctggctca       3540
caaataccac tgagatcttt ttccctctgc caaaaattat ggggacatca tgaagcccct       3600
tgagcatctg acttctggct aataaaggaa atttattttc attgcaatag tgtgttggaa       3660
ttttttgtgt ctctcactcg gaaggacata tgggagggca atcatttaa  aacatcagaa       3720 tgagtatttg gtttagagtt tggcaacata tgcccatatg ctggctgcca tgaacaaagg       3780
ttggctataa agaggtcatc agtatatgaa acagcccct  gctgtccatt ccttattcca       3840
tagaaaagcc ttgacttgag gttagatttt ttttatattt tgttttgtgt tattttttc        3900 tttaacatcc ctaaaatttt ccttacatgt tttactagcc agattttcc  tcctctcctg       3960 actactccca gtcatagctg tccctcttct cttatggaga tccctcgacc tgcagcccaa       4020
gctgtagata agtagcatgg cgggttaatc attaactaca aggaacccct agtgatggag       4080
ttggccactc cctctctgcg cgctcgctcg ctcactgagg ccgggcgacc aaaggtcgcc       4140
cgacgcccgg gctttgcccg gcggcctca  gtgagcgagc gagcgcgcag ctgcattaat       4200
gaatcggcca acgcgcgggg agaggcggtt tgcgtattgg gcgctcttcc gcttcctcgc       4260
tcactgactc gctgcgctcg tcgttcggc  tgcggcgagc ggtatcagct cactcaaagg       4320
cggtaatacg gttatccaca gaatcagggg ataacgcagg aaagaacatg tgagcaaaag       4380
gccagcaaaa ggccaggaac cgtaaaaagg ccgcgttgct ggcgtttttc cataggctcc       4440
gcccccctga cgagcatcac aaaaatcgac gctcaagtca gaggtggcga aacccgacag       4500
gactataaag ataccaggcg tttccccctg gaagctccct cgtgcgctct cctgttccga       4560
ccctgccgct taccggatac ctgtccgcct ttctcccttc gggaagcgtg cgctttctc       4620 atagctcacg ctgtaggtat ctcagttcgg tgtaggtcgt tcgctccaag ctgggctgtg       4680
tgcacgaacc ccccgttcag cccgaccgct gcgccttatc cggtaactat cgtcttgagt       4740
ccaacccggt aagacacgac ttatcgccac tggcagcagc cactggtaac aggattagca       4800
gagcgaggta tgtaggcggt gctacagagt tcttgaagtg gtggcctaac tacggctaca       4860
ctagaagaac agtatttggt atctgcgctc tgctgaagcc agttaccttc ggaaaaagag       4920
ttggtagctc ttgatccggc aaacaaacca ccgctggtag cggtggtttt tttgtttgca       4980
agcagcagat tacgcgcaga aaaaaaggat ctcaagaaga tcctttgatc ttttctacgg       5040
ggtctgacgc tcagtggaac gaaaactcac gttaagggat tttggtcatg agattatcaa       5100
aaaggatctt cacctagatc cttttaaatt aaaaatgaag ttttaaatca atctaaagta       5160
tatatgagta aacttggtct gacagttacc aatgcttaat cagtgaggca cctatctcag       5220
cgatctgtct atttcgttca tccatagttg cctgactccc cgtcgtgtag ataactacga       5280
tacgggaggg cttaccatct ggccccagtg ctgcaatgat accggggtta acgcgaattt       5340
taacaaaata ttaacgctta caatttaggt ggcacttttc ggggaaatgt gcgcggaacc       5400
cctatttgtt tatttttcta aatacattca aatatgtatc cgctcatgag acaataaccc       5460
```

```
tgataaatgc ttcaataata ttgaaaaagg aagagtatga ttgaacagga tggcctgcat    5520
gcgggtagcc cggcagcgtg ggtggaacgt ctgtttggct atgattgggc gcagcagacc    5580
attggctgct ctgatgcggc ggtgtttcgt ctgagcgcgc agggtcgtcc ggtgctgttt    5640
gtgaaaaccg atctgagcgg tgcgctgaac gagctgcagg atgaagcggc gcgtctgagc    5700
tggctggcca ccaccggtgt tccgtgtgcg gcggtgctgg atgtggtgac cgaagcgggc    5760
cgtgattggc tgctgctggg cgaagtgccg ggtcaggatc tgctgtctag ccatctggcg    5820
ccggcagaaa aagtgagcat tatggcggat gccatgcgtc gtctgcatac cctggacccg    5880
gcgacctgtc cgtttgatca tcaggcgaaa catcgtattg aacgtgcgcg tacccgtatg    5940
gaagcgggcc tggtggatca ggatgatctg gatgaagaac atcagggcct ggcaccggca    6000
gagctgtttg cgcgtctgaa agcgagcatg ccggatggcg aagatctggt ggtgacccat    6060
ggtgatgcgt gcctgccgaa cattatggtg gaaaatggcc gttttagcgg ctttattgat    6120
tgcggccgtc tgggcgtggc ggatcgttat caggatattg cgctggccac ccgtgatatt    6180
gcggaagaac tgggcggcga atgggcggat cgttttctgg tgctgtatgg cattgcggca    6240
ccggatagcc agcgtattgc gttttatcgt ctgctggatg aatttttcta ataactgtca    6300
gaccaagttt actcatatat actttagatt gatttaaaac ttcattttta atttaaaaca    6360
attggatggg caattggata tcgtcatctt tgagacacaa tctcccacct cactggaatt    6420
tagttcctgc tataattagc cttcctcata agttgcacta cttcagcgtc ccatatgcac    6480
ccttaccacg aagacaggtt tgtccaatcc catattgcga ccttggcagg gggttcgcaa    6540
gtcccacccg aaacgttgct gaaggctcag gtttctgagc gacaaaaggt taatacgcga    6600
gttcccgctc ataacctgga ccgaatgcgg aatcatgcat cgttccactg tgtttgtctc    6660
atgtaggacg ggcgcaaagc atacttagtt caatcttgaa taccttatat tattgtacac    6720
ctaccggtca ccagccaaca atgtgcggac ggcgttgcaa cttcagggc ctaatctgac    6780 cgttgtagat accgcactct gggcaatacg aggtaatgcc agtcacccag tgtcgaacaa    6840
cacctgacct aacggtaaga ggctcacata atggctctgc cggcgtgccc agggtatatt    6900
aggtcagcat cagatggact gacatgaatc tttacaccga agcggaaacg ggtgcgtgga    6960
ctagcgagga gcaaacgaaa attcctggcc tgcttgatgt ctcgtaatct tcttagagat    7020
ggacgaaatg tttcacgacc taggaaaagg tcgccctaca aaatagattt gcgttactct    7080
cttcatagga tccccggtgt agcgaaagat caaggcgacc ctaggtagca accgccggct    7140
tcggcggtaa ggtatcactc aagaagcaga ctcagtaaga cacggtctag ctgactgtct    7200
atcgcctagg tcaaatatggg agctttgatt ctgcatgtcc agctttagat tcactttagc    7260
gcgcagatct gggtcgagat aaaatcacca gtacccaaga ccaggggggc tcgccgcgtt    7320
ggctaatcct ggtacatctt gtaatgaata ttcagtagaa aatttgtgtt agaaggacga    7380
gtcaccatgt accaaaagcg ataacgatcg gtgggagtat tcattgtggt gaagacgctg    7440
ggtttacgtg ggaaaggtgc ttgtgtccca acaggctagg atataatgct gaagcccttc    7500
cccaagcgtt cagggtggga tttgctacaa cttccgagtc caacgtgtcc gtgttcatgt    7560
tatatatgca caaggccgag aattggacgt agctttcgtg ttagtacgta gcatggtcac    7620
acaagcacag tagatcctgc ccgcgcatcc tatatattaa gttaattcta atggaatacg    7680
atgacatgtg gatgggcagt ggccggttgt tacacgccta ccgcgatgct gaatgacccg    7740
gactaaagtg gcgaaaatta tggcgtgtga cccgttatgc tccagttcgg tcagtgggtc    7800
```

```
attgcaagta gtcgattgca ttgtcaatct ccgagtgatt tagcgtgaca gccgcaggga    7860
acccataaaa tgcgatcgta gtccatccga tcgtacatag aaatgagggt ccccatacgc    7920
ccacgcacct gttcactcgt cgtttgcatt taagagccgc acgaaccaca gagcataaag    7980
aggacctcta gctcctttac aaagtggggt cgaccgatcg cttgcgcaac ttgtgaagtg    8040
tctaccatcc ctaagcccat ttcccgcata ttaacccctg attgtatccg catctgatgc    8100
taccgtggtt gagttagcgt cgagcacgcg ggacttattg catgagtaga gttgactaag    8160
agccgttaga tggctcgctg agctaatagt tgccgacaga tcgtcaagat tagaaaacgg    8220
ttgtagcatt atcggaggtt ctctaactag tatcgatagc cgtgtcttca ctgtgccgcg    8280
gctacctatc gcctgaaaac cagttggtgt taaggggtcc cctgtccagg acgccaccgg    8340
tagtgagaca tacacgttcg ttgggttcac cgcggtcgga cctgagtgca ccaaggacac    8400
actgcagctc cgacccctac tgtcgagaaa tttgtatccc gcccccgcag cttgccagct    8460
ctttcagtat catggagccc atggttgaat gagtccaata acgaacttcg acatgataaa    8520
atccccccct cgcgacttcc agagaagaag actactgact tgagcgttcc cagcacttca    8580
gccaaggaag ttaccaattt tttgtttccg aatgacaccg gtctccttgc gggtagatcg    8640
ccgaccgcag aacttacgag ccaggggaaa cagtaaggcc taattaggta aagggagtaa    8700
gtgctcgaac gcttcagatg taaccatata cttacgctgg atcttctccc gcgaatttta    8760
accctcacca actacgagat ttgaggtaaa ccaaataagc acgtagtggc gctatccgac    8820
tgttcccaaa ttgtaactta tcgttccgtg aaggccagag ttacttcccg gcccttttcca   8880 tgcgcgcacc atacccttcct agttccccgg ttatctctcc gaggagggag tgagcgatcc    8940
tccgtttacg ttttgttacc aatgacgtag ctatgtattt tgtacaggtt gccaacgggt    9000
ttcacaattc acagatagtg gggtacccgg caaagggcct atatttgcgg tccaacttag    9060
gcgtaaacta cgatggtacc tactcagacc cagctcgcgc ggcgtaaata acgcactcat    9120
cccagctgat tctcggcgat ctacgcagcg acatgattat caacagctgt ctggcagctc    9180
taatctttta ccatggtcgt aaaagcctcc aagagttaga tcatacctaa cgccacaaaa    9240
gtgacacgac gccgatgggt accggacttt aggtgcacca cagttcggta agggagaggc    9300
cctgcggcgt acttcatttt gtatatgcaa cgtgcccaag tggcgccagg caagtctcag    9360
ctggttcctg tgttagctgc aggctaggca tgggagctga ttgaacatgg gttgggggcc    9420
tcgaaccgtc gaggaccccca tagtacgttt aaacccaagt agggcagcct atagtttgaa   9480
gcagtactat ttcagggggg gagccctcat ggtctcttct actgatgact caacacgcta    9540
gggacgtgaa gtcgattcct tcgatggtta taaatcaaag gctcagagtg cagtctggag    9600
cgccatctca acggtacgca tctcgattgc tcggtcgcct ttcacactcc gcgaaaattc    9660
ataccgctca ttcactaggt tgcgaagcct acactgatat atgaatccaa gctagagcag    9720
ggctcttaaa attcggagtt gtagatgctc aatactccaa tcggtttttt cgtgcaccac    9780
cgcgggtggc tgacaagggt ttgacatcga gaaacaaggc agttccgggc tgaaagtagc    9840
gccgggtaag gtacgcgcct ggtatggcag gactatgaag ccaatacaaa ggctacatcc    9900
tcactcgggt ggacggaaac gcagaattat ggttactttt tggatacgtg aaacatgtcc    9960
catggtagcc caaagacttg ggagtctatc accccctaggg cccatttctg gatatagacg   10020
ccaggttgaa tccgtatttg gaggtacgat ggatcagtct gggtgggacg tgctccattt   10080
ataccctgcg caggctggac cgaggaccgc aagatgcgac ggtgcacaag taattgacaa   10140
caaaccatcg tgttttcatt atggtaccag gatcttcaag ccgagtcaat caagctcgga   10200
```

```
ttacagtgtt taccgcgtct tgcggttact cacaaactgt aatccaccac aagtcaagcc    10260
attgcctctc tgagacgccg tatgaattaa tatgtaaact ttgcgcgggt tcactgcgat    10320
ccgttcagtc tcgtccaagg gcacaatcga attcccattt gtatgttcgg ctaacttcta    10380
cccatccccc gaagtttagc aggtcgtgag gtgtcatgga ggctctcgtt catcccgtgg    10440
gacatcgttt aaacgccttg ataaagcacc ccgctcgggt gtagcagaga agacgcctac    10500
tgaattgtgc gatccctcca cctcagctaa ggtagctacc aatatttagt tttttagcct    10560
tgcgacagac ctcctactta gattgccacg cattgagcta gcgagtcagc gataagcatg    10620
acgcgctttc aagcgtcgcg agtatgtgaa ccaaggctcc ggacaggact atatacttgg    10680
gtttgatctc gccccgacaa ctgcaaacct caacatttat agattataag gttagccgaa    10740
attgcacgtg gtggcgcccg ccgactgctc cccgagtgtg gctctttgat ctgacaacgc    10800
gcgacctcca tcgcggccga ttgtttctgc ggaccatgtc gtcctcatag tttgggcatg    10860
tttccgttgt aggagtgaag ccacttagct ttgcgccgta gtcccaatga aaaacctatg    10920
gactttgttt tgggtagcat caggaatctg aaccctgtga atgtgggggt cgcgcgcata    10980
gacctttatc tccggttcaa gttaggcatg aggctgtcga cccctaatca gtgaggccac    11040
cgagtaaaag agtctgtcca tcacgcaaat taaccgttgt cgcaatactt ctttgattag    11100
taataacatc acttgcctga gtagaagaac tcaaactatc ggccttgctg gtaatatcca    11160
gaacaatatt accgccagcc attgcaacgg aatcgccatt cgccattcag gctgcgcaac    11220
tgttgggaag ggcgatcggt gcgggcctct tcgct                              11255
```

<210> SEQ ID NO 3
<211> LENGTH: 11396
<212> TYPE: DNA
<213> ORGANISM: Artificial Sequence
<220> FEATURE:
<223> OTHER INFORMATION: Plasmid pohIDS-874

<400> SEQUENCE: 3

```
attacgccag ctgcgcgctc gctcgctcac tgaggccgcc cgggcaaagc ccgggcgtcg     60
ggcgaccttt ggtcgcccgg cctcagtgag cgagcgagcg cgcagagagg gagtggccaa    120
ctccatcact aggggttcct tgtagttaat gattaacccg ccatgctact tatctactcg    180
acattgatta ttgactagtt attaatagta atcaattacg gggtcattag ttcatagccc    240
atatatggag ttccgcgtta cataacttac ggtaaatggc ccgcctggct gaccgcccaa    300
cgacccccgc ccattgacgt caataatgac gtatgttccc atagtaacgc caatagggac    360
tttccattga cgtcaatggg tggagtattt acggtaaact gcccacttgg cagtacatca    420
agtgtatcat atgccaagta cgccccctat tgacgtcaat gacggtaaat ggcccgcctg    480
gcattatgcc cagtacatga ccttatggga ctttcctact tggcagtaca tctacgtatt    540
agtcatcgct attaccatgg tcgaggtgag ccccacgttc tgcttcactc tccccatctc    600
cccccctcc ccacccccaa ttttgtattt atttattttt aattattttt gtgcagcgat    660
gggggcgggg ggggggggg ggcgcgcgcc aggcggggcg gggcggggcg aggggcgggg    720
cggggcgagg cggagaggtg cggcggcagc caatcagagc ggcgcgctcc gaaagtttcc    780
ttttatggcg aggcggcggc ggcggcggcc ctataaaaag cgaagcgcgc ggcgggcggg    840
agtcgctgcg cgctgccttc gccccgtgcc ccgctccgcc gccgcctcgc gccgcccgcc    900
ccggctctga ctgaccgcgt tactcccaca ggtgagcggg cggacggcc cttctcctcc    960
```

-continued

```
gggctgtaat tagcgcttgg tttaatgacg gcttgtttct tttctgtggc tgcgtgaaag    1020
ccttgagggg ctccgggagg gcccttttgtg cggggggagc ggctcggggg gtgcgtgcgt    1080
gtgtgtgtgc gtggggagcg ccgcgtgcgg ctccgcgctg cccggcggct gtgagcgctg    1140
cgggcgcggc gcggggcttt gtgcgctccg cagtgtgcgc gaggggagcg cggccggggg    1200
cggtgccccg cggtgcgggg ggggctgcga ggggaacaaa ggctgcgtgc ggggtgtgtg    1260
cgtggggggg tgagcagggg gtgtgggcgc gtcggtcggg ctgcaacccc ccctgcaccc    1320
ccctccccga gttgctgagc acggcccggc ttcgggtgcg gggctccgta cggggcgtgg    1380
cgcggggctc gccgtgccgg gcggggggtg cggcaggtg ggggtgccgg gcggggcggg    1440
gccgcctcgg gccggggagg gctcggggga ggggcgcggc ggccccccgga gcgccggcgg    1500
ctgtcgaggc gcggcgagcc gcagccattg ccttttatgg taatcgtgcg agagggcgca    1560
gggacttcct ttgtcccaaa tctgtgcgga gccgaaatct gggaggcgcc gccgcaccccc    1620
ctctagcggg cgcggggcga agcggtgcgg cgccggcagg aaggaaatgg gcggggaggg    1680
ccttcgtgcg tcgccgcgcc gccgtcccct tctccctctc cagcctcggg gctgtccgcg    1740
gggggacggc tgccttcggg ggggacgggg cagggcgggg ttcggcttct ggcgtgtgac    1800
cggcggctct agagcctctg ctaaccatgt tcatgccttc ttcttttttcc tacagctcct    1860
gggcaacgtg ctggttattg tgctgtctca tcattttggc aaagaattga ttaattcgag    1920
cgaacgcgtg ccaccatgcc cccacctaga accggaagag gattgctctg gctcggactt    1980
gtgctgtcca gcgtgtgtgt ggccctgggc tcggaaaccc aggccaacag caccaccgac    2040
gccctgaatg tgctgctgat tatcgtggac gatctccggc cttcgctggg ctgctacggg    2100
gataagctgg tccgctcccc gaatatcgac caactggctt cacatagcct gcttttccaa    2160
aacgcattcg cccaacaagc cgtgtgcgcc ccgagccgcg tgtctttcct caccggccgg    2220
cgccctgata ctacccggct ctacgacttc aacagctact ggagagtgca cgcaggaaac    2280
ttctccacca ttcctcagta cttttaaggag aacggttacg tcaccatgag cgtggggaag    2340
gtgttccacc ctggaatttc ctccaaccac accgacgact cgccatactc ctggtccttt    2400
cccccttacc acccatcatc cgagaagtac gagaacacca agacgtgcag gggcccagac    2460
ggggaactgc acgcgaacct cctctgcccg gtcgatgtgc tggatgtgcc cgaaggcacc    2520
ctccctgaca aacagagcac cgaacaggcc atccagctcc tcgagaagat gaaaacttca    2580
gcctccccgt tctttctggc cgtgggatac cacaagccgc atatcccctt ccggtaccca    2640
aaggagttcc agaagctgta cccgctggag aacattaccc tggctcctga tcccgaagtg    2700
ccggacggcc tgccgcccgt ggcatacaac ccttggatgg acatccgcca gagggaggat    2760
gtgcaagccc tgaacatctc cgtgccatac ggtccgatcc cggtcgactt ccagcggaag    2820
attaggcagt catatttcgc gtccgtgtcc tacttggaca ctcaggtcgg acgcctcctc    2880
tccgctctcg acgatctgca gctggccaac tcgaccatta tcgcgttcac ctcggaccat    2940
ggttgggctc tgggcgaaca cggagaatgg gccaagtaca gcaatttcga tgtcgcgact    3000
cacgtgcccc tgatcttcta cgtgcccgga cgcacagcca gcttgcctga agcggggaa    3060
aagctgttcc cttacctgga tcccttcgac tccgcctctc aacttatgga gccaggcaga    3120
cagtcgatgg acctggtgga actcgtgtca ctgttcccta ccctcgccgg tctggccgga    3180
cttcaggtcc cgcctcggtg cccggtgccg tccttccacg tggagctgtg tcgcgaggga    3240
aagaacctcg tgaaacactt ccggttccgc gacctggagg aagatcccta cttgccgggc    3300
aacccgagag aacttatcgc atactcccag taccctcgcc cctccgacat cccgcagtgg    3360
```

```
aactccgaca agccgagcct gaaggacatt aagatcatgg ggtactccat ccggactatt    3420
gactatcggt acactgtgtg ggtcgggttc aacccagatg agtttctggc caacttctcc    3480
gatatccatg ccggagagct gtacttcgtg gactcggacc cgctgcagga ccacaacatg    3540
tacaacgact cacagggcgg cgacctgttc cagttgctga tgccctgaga attcgagctc    3600
ggtacccggg aatcaattca ctcctcaggt gcaggctgcc tatcagaagg tggtggctgg    3660
tgtggccaat gccctggctc acaaatacca ctgagatctt tttccctctg ccaaaaatta    3720
tggggacatc atgaagcccc ttgagcatct gacttctggc taataaagga aatttatttt    3780
cattgcaata gtgtgttgga attttttgtg tctctcactc ggaaggacat atgggagggc    3840
aaatcattta aaacatcaga atgagtattt ggtttagagt ttggcaacat atgcccatat    3900
gctggctgcc atgaacaaag gttggctata aagaggtcat cagtatatga acagccccc    3960 tgctgtccat tccttattcc atagaaaagc cttgacttga ggttagattt tttttatatt    4020
ttgttttgtg ttattttttt ctttaacatc cctaaaattt tccttacatg ttttactagc    4080
cagatttttc ctcctctcct gactactccc agtcatagct gtccctcttc tcttatggag    4140
atccctcgac ctgcagccca agctgtagat aagtagcatg gcgggttaat cattaactac    4200 aaggaaccc tagtgatgga gttggccact ccctctctgc gcgctcgctc gctcactgag    4260
gccgggcgac caaggtcgcc cgacgcccg ggctttgccc gggcggcctc agtgagcgag    4320
cgagcgcgca gctgcattaa tgaatcggcc aacgcgcggg gagaggcggt ttgcgtattg    4380
ggcgctcttc cgcttcctcg ctcactgact cgctgcgctc ggtcgttcgg ctgcggcgag    4440
cggtatcagc tcactcaaag gcggtaatac ggttatccac agaatcaggg gataacgcag    4500
gaaagaacat gtgagcaaaa ggccagcaaa aggccaggaa ccgtaaaaag gccgcgttgc    4560
tggcgttttt ccataggctc cgcccccctg acgagcatca caaaaatcga cgctcaagtc    4620
agaggtggcg aaacccgaca ggactataaa gataccaggc gtttccccct ggaagctccc    4680
tcgtgcgctc tcctgttccg accctgccgc ttaccggata cctgtccgcc tttctccctt    4740
cgggaagcgt ggcgctttct catagctcac gctgtaggta tctcagttcg gtgtaggtcg    4800
ttcgctccaa gctgggctgt gtgcacgaac cccccgttca gcccgaccgc tgcgccttat    4860
ccggtaacta tcgtcttgag tccaacccgg taagacacga cttatcgcca ctggcagcag    4920
ccactggtaa caggattagc agagcgaggt atgtaggcgg tgctacagag ttcttgaagt    4980
ggtggcctaa ctacggctac actagaagaa cagtatttgg tatctgcgct ctgctgaagc    5040
cagttacctt cggaaaaaga gttggtagct cttgatccgg caaacaaacc accgctggta    5100
gcggtggttt ttttgtttgc aagcagcaga ttacgcgcag aaaaaaagga tctcaagaag    5160
atcctttgat cttttctacg gggtctgacg ctcagtggaa cgaaaactca cgttaaggga    5220
ttttggtcat gagattatca aaaaggatct tcacctagat ccttttaaat taaaaatgaa    5280
gttttaaatc aatctaaagt atatatgagt aaacttggtc tgacagttac caatgcttaa    5340
tcagtgaggc acctatctca gcgatctgtc tatttcgttc atccatagtt gcctgactcc    5400
ccgtcgtgta gataactacg atacgggagg gcttaccatc tggccccagt gctgcaatga    5460
taccggggtt aacgcgaatt ttaacaaaat attaacgctt acaatttagg tggcacttt    5520 cggggaaatg tgcgcggaac ccctatttgt ttatttttct aaatacattc aaatatgtat    5580
ccgctcatga caataaacc ctgataaatg cttcaataat attgaaaaag gaagagtatg    5640
attgaacagg atggcctgca tgcgggtagc ccggcagcgt gggtggaacg tctgtttggc    5700
```

-continued

```
tatgattggg cgcagcagac cattggctgc tctgatgcgg cggtgtttcg tctgagcgcg    5760
cagggtcgtc cggtgctgtt tgtgaaaacc gatctgagcg gtgcgctgaa cgagctgcag    5820
gatgaagcgg cgcgtctgag ctggctggcc accaccggtg ttccgtgtgc ggcggtgctg    5880
gatgtggtga ccgaagcggg ccgtgattgg ctgctgctgg gcgaagtgcc gggtcaggat    5940
ctgctgtcta gccatctggc gccggcagaa aaagtgagca ttatggcgga tgccatgcgt    6000
cgtctgcata ccctggaccc ggcgacctgt ccgtttgatc atcaggcgaa acatcgtatt    6060
gaacgtgcgc gtacccgtat ggaagcgggc ctggtggatc aggatgatct ggatgaagaa    6120
catcagggcc tggcaccggc agagctgttt gcgcgtctga agcgagcat gccggatggc    6180 gaagatctgg tggtgaccca tggtgatgcg tgcctgccga acattatggt ggaaaatggc    6240
cgttttagcg gctttattga ttgcggccgt ctgggcgtgg cggatcgtta tcaggatatt    6300
gcgctggcca cccgtgatat tgcggaagaa ctgggcggcg aatgggcgga tcgttttctg    6360
gtgctgtatg gcattgcggc accgatagc cagcgtattg cgttttatcg tctgctggat    6420 gaattttct aataactgtc agaccaagtt tactcatata tacttagat tgattaaaa    6480 cttcatttt aatttaaaac aattggatgg gcaattggat atcgtcatct ttgagacaca    6540
atctcccacc tcactggaat ttagttcctg ctataattag ccttcctcat aagttgcact    6600
acttcagcgt cccatatgca cccttaccac gaagacaggt ttgtccaatc ccatattgcg    6660
accttggcag ggggttcgca agtcccaccc gaaacgttgc tgaaggctca ggtttctgag    6720
cgacaaaagg ttaatacgcg agttcccgct cataacctgg accgaatgcg gaatcatgca    6780
tcgttccact gtgtttgtct catgtaggac gggcgcaaag catacttagt tcaatcttga    6840 atacctata ttattgtaca cctaccggtc accagccaac aatgtgcgga cggcgttgca    6900
actttcaggg cctaatctga ccgttgtaga taccgcactc tgggcaatac gaggtaatgc    6960
cagtcaccca gtgtcgaaca acacctgacc taacggtaag aggctcacat aatggctctg    7020
ccggcgtgcc cagggtatat taggtcagca tcagatggac tgacatgaat ctttacaccg    7080
aagcggaaac gggtgcgtgg actagcgagg agcaaacgaa aattcctggc ctgcttgatg    7140
tctcgtaatc ttcttagaga tggacgaaat gtttcacgac ctaggaaaag gtcgccctac    7200
aaaatagatt tgcgttactc tcttcatagg atccccggtg tagcgaaaga tcaaggcgac    7260
cctaggtagc aaccgccggc ttcggcggta aggtatcact caagaagcag actcagtaag    7320
acacggtcta gctgactgtc tatcgcctag gtcaaatagg gagctttgat tctgcatgtc    7380
cagctttaga ttcactttag cgcgcagatc tgggtcgaga taaaatcacc agtacccaag    7440
accagggggg ctcgccgcgt tggctaatcc tggtacatct tgtaatgaat attcagtaga    7500
aaatttgtgt tagaaggacg agtcaccatg taccaaaagc gataacgatc ggtgggagta    7560
ttcattgtgg tgaagacgct gggtttacgt gggaaaggtg cttgtgtccc aacaggctag    7620
gatataatgc tgaagcccctt ccccaagcgt tcagggtggg atttgctaca acttccgagt    7680
ccaacgtgtc cgtgttcatg ttatatatgc acaaggccga gaattggacg tagctttcgt    7740
gttagtacgt agcatggtca cacaagcaca gtagatcctg cccgcgcatc ctatatatta    7800
agttaattct aatggaatac gatgacatgt ggatgggcag tggccggttg ttacacgcct    7860
accgcgatgc tgaatgaccc ggactaaagt ggcgaaaatt atggcgtgtg accgttatg    7920 ctccagttcg gtcagtgggt cattgcaagt agtcgattgc attgtcaatc tccgagtgat    7980
ttagcgtgac agccgcaggg aacccataaa atgcgatcgt agtccatccg atcgtacata    8040
gaaatgaggg tccccatacg cccacgcacc tgttcactcg tcgtttgcat ttaagagccg    8100
```

```
cacgaaccac agagcataaa gaggacctct agctccttta caaagtgggg tcgaccgatc   8160
gcttgcgcaa cttgtgaagt gtctaccatc cctaagccca tttcccgcat attaacccct   8220
gattgtatcc gcatctgatg ctaccgtggt tgagttagcg tcgagcacgc gggacttatt   8280
gcatgagtag agttgactaa gagccgttag atggctcgct gagctaatag ttgccgacag   8340
atcgtcaaga ttagaaaacg gttgtagcat tatcggaggt tctctaacta gtatcgatag   8400
ccgtgtcttc actgtgccgc ggctacctat cgcctgaaaa ccagttggtg ttaaggggtc   8460
ccctgtccag gacgccaccg gtagtgagac atacacgttc gttgggttca ccgcggtcgg   8520
acctgagtgc accaaggaca cactgcagct ccgacccta ctgtcgagaa atttgtatcc   8580
cgcccccgca gcttgccagc tctttcagta tcatggagcc catggttgaa tgagtccaat   8640
aacgaacttc gacatgataa aatcccccc tcgcgacttc cagagaagaa gactactgac   8700
ttgagcgttc ccagcacttc agccaaggaa gttaccaatt ttttgtttcc gaatgacacc   8760
ggtctccttg cgggtagatc gccgaccgca gaacttacga gccaggggaa acagtaaggc   8820
ctaattaggt aaagggagta agtgctcgaa cgcttcagat gtaaccatat acttacgctg   8880
gatcttctcc cgcgaatttt aaccctcacc aactacgaga tttgaggtaa accaaataag   8940
cacgtagtgg cgctatccga ctgttcccaa attgtaactt atcgttccgt gaaggccaga   9000
gttacttccc ggccctttcc atgcgcgcac catacctcc tagttccccg gttatctctc   9060
cgaggaggga gtgagcgatc ctccgtttac gttttgttac caatgacgta gctatgtatt   9120
ttgtacaggt tgccaacggg tttcacaatt cacagatagt ggggtacccg gcaaagggcc   9180
tatatttgcg gtccaactta ggcgtaaact acgatggtac ctactcagac ccagctcgcg   9240
cggcgtaaat aacgcactca tcccagctga ttctcggcga tctacgcagc gacatgatta   9300
tcaacagctg tctggcagct ctaatctttt accatggtcg taaaagcctc caagagttag   9360
atcataccta acgccacaaa agtgacacga cgccgatggg taccggactt taggtgcacc   9420
acagttcggt aagggagagg ccctgcggcg tacttcattt tgtatatgca acgtgcccaa   9480
gtggcgccag gcaagtctca gctggttcct gtgttagctg caggctaggc atgggagctg   9540
attgaacatg ggttgggggc ctcgaaccgt cgaggacccc atagtacgtt taaacccaag   9600
tagggcagcc tatagtttga agcagtacta tttcaggggg ggagccctca tggtctcttc   9660
tactgatgac tcaacacgct agggacgtga agtcgattcc ttcgatggtt ataaatcaaa   9720
ggctcagagt gcagtctgga gcgcccatct aacggtacgc atctcgattg ctcggtcgcc   9780
tttcacactc cgcgaaaatt cataccgctc attcactagg ttgcgaagcc tacactgata   9840
tatgaatcca agctagagca gggctcttaa aattcggagt tgtagatgct caatactcca   9900
atcggttttt tcgtgcacca ccgcgggtgg ctgacaaggg tttgacatcg agaaacaagg   9960
cagttccggg ctgaaagtag cgccgggtaa ggtacgcgcc tggtatggca ggactatgaa  10020
gccaatacaa aggctacatc ctcactcggg tggacgaaa cgcagaatta tggttacttt  10080
ttggatacgt gaaacatgtc ccatggtagc ccaaagactt gggagtctat caccctagg  10140 gcccatttct ggatatagac gccaggttga atccgtattt ggaggtacga tggatcagtc  10200
tgggtgggac gtgctccatt tatacctgc gcaggctgga ccgaggaccg caagatgcga  10260
cggtgcacaa gtaattgaca acaaaccatc gtgttttcat tatggtacca ggatcttcaa  10320
gccgagtcaa tcaagctcgg attacagtgt ttaccgcgtc ttgcggttac tcacaaactg  10380
taatccacca caagtcaagc cattgcctct ctgagacgcc gtatgaatta atatgtaaac  10440
```

| | | | | |
|---|---|---|---|---|
| tttgcgcggg | ttcactgcga | tccgttcagt | ctcgtccaag | ggcacaatcg aattcccatt | 10500 |
| tgtatgttcg | gctaacttct | acccatcccc | cgaagtttag | caggtcgtga ggtgtcatgg | 10560 |
| aggctctcgt | tcatcccgtg | ggacatcgtt | taaacgcctt | gataaagcac cccgctcggg | 10620 |
| tgtagcagag | aagacgccta | ctgaattgtg | cgatccctcc | acctcagcta aggtagctac | 10680 |
| caatatttag | ttttttagcc | ttgcgacaga | cctcctactt | agattgccac gcattgagct | 10740 |
| agcgagtcag | cgataagcat | gacgcgcttt | caagcgtcgc | gagtatgtga accaaggctc | 10800 |
| cggacaggac | tatatacttg | ggtttgatct | cgccccgaca | actgcaaacc tcaacattta | 10860 |
| tagattataa | ggttagccga | aattgcacgt | ggtggcgccc | gccgactgct ccccgagtgt | 10920 |
| ggctctttga | tctgacaacg | cgcgacctcc | atcgcggccg | attgtttctg cggaccatgt | 10980 |
| cgtcctcata | gtttgggcat | gttttccgttg | taggagtgaa | gccacttagc tttgcgccgt | 11040 |
| agtcccaatg | aaaaacctat | ggactttgtt | ttgggtagca | tcaggaatct gaaccctgtg | 11100 |
| aatgtggggg | tcgcgcgcat | agacctttat | ctccggttca | agttaggcat gaggctgtcg | 11160 |
| accccctaatc | agtgaggcca | ccgagtaaaa | gagtctgtcc | atcacgcaaa ttaaccgttg | 11220 |
| tcgcaatact | tctttgatta | gtaataacat | cacttgcctg | agtagaagaa ctcaaactat | 11280 |
| cggccttgct | ggtaatatcc | agaacaatat | taccgccagc | cattgcaacg gaatcgccat | 11340 |
| tcgccattca | ggctgcgcaa | ctgttgggaa | gggcgatcgg | tgcgggcctc ttcgct | 11396 |

<210> SEQ ID NO 4
<211> LENGTH: 6630
<212> TYPE: DNA
<213> ORGANISM: Artificial Sequence
<220> FEATURE:
<223> OTHER INFORMATION: Plasmid pRepCap9-808

<400> SEQUENCE: 4

| | | | | |
|---|---|---|---|---|
| ctaaattgta | agcgttaata | ttttgttaaa | attcgcgtta | aattttgtt aaatcagctc | 60 |
| atttttaac | caataggccg | aaatcggcaa | aatcccttat | aaatcaaaag aatagaccga | 120 |
| gatagggttg | agtggccgct | acagggcgct | cccattcgcc | attcaggctg cgcaactgtt | 180 |
| gggaagggcg | tttcggtgcg | ggcctcttcg | ctattacgcc | agctggcgaa agggggatgt | 240 |
| gctgcaaggc | gattaagttg | ggtaacgcca | gggttttccc | agtcacgacg ttgtaaaacg | 300 |
| acggccagtg | agcgcgacgt | aatacgactc | actatagggc | gaattggcgg aaggccgtca | 360 |
| aggccgcatc | ccggggcggc | cgcgaggtcc | tgtattagag | gtcacgtgag tgttttgcga | 420 |
| cattttgcga | caccatgtgg | tcacgctggg | tatttaagcc | cgagtgagca cgcagggtct | 480 |
| ccatttgaa | gcgggaggtt | tgaacgcgca | gccgccatgc | cggggtttta cgagattgtg | 540 |
| attaaggtcc | ccagcgacct | tgacgagcat | ctgcccggca | tttctgacag ctttgtgaac | 600 |
| tgggtggccg | agaaggaatg | ggagttgccg | ccagattctg | acatggatct gaatctgatt | 660 |
| gagcaggcac | ccctgaccgt | ggccgagaag | ctgcagcgcg | actttctgac ggaatggcgc | 720 |
| cgtgtgagta | aggcccccgga | ggccctttttc | tttgtgcaat | ttgagaaggg agagagctac | 780 |
| ttccacatgc | acgtgctcgt | ggaaaccacc | ggggtgaaat | ccatggtttt gggacgtttc | 840 |
| ctgagtcaga | ttcgcgaaaa | actgattcag | agaatttacc | gcgggatcga gccgactttg | 900 |
| ccaaactggt | tcgcggtcac | aaagaccaga | aatggcgccg | gaggcgggaa caaggtggtg | 960 |
| gatgagtgct | acatccccaa | ttacttgctc | cccaaaaccc | agcctgagct ccagtgggcg | 1020 |
| tggactaata | tggaacagta | tttaagcgcc | tgtttgaatc | tcacggagcg taaacggttg | 1080 |
| gtggcgcagc | atctgacgca | cgtgtcgcag | acgcaggagc | agaacaaaga gaatcagaat | 1140 |

-continued

```
cccaattctg atgcgccggt gatcagatca aaaacttcag ccaggtacat ggagctggtc    1200
gggtggctcg tggacaaggg gattacctcg agaagcagt ggatccagga ggaccaggcc     1260
tcatacatct ccttcaatgc ggcctccaac tcgcggtccc aaatcaaggc tgccttggac    1320
aatgcgggaa agattatgag cctgactaaa accgccccg actacctggt gggccagcag    1380
cccgtggagg acatttccag caatcggatt tataaaattt tggaactaaa cgggtacgat    1440
ccccaatatg cggcttccgt ctttctggga tgggccacga aaaagttcgg caagaggaac    1500
accatctggc tgtttgggcc tgcaactacc gggaagacca catcgcgga ggccatagcc     1560 cacactgtgc ccttctacgg gtgcgtaaac tggaccaatg agaactttcc cttcaacgac    1620
tgtgtcgaca agatggtgat ctggtgggag gaggggaaga tgaccgccaa ggtcgtggag    1680
tcggccaaag ccattctcgg aggaagcaag gtgcgcgtgg accagaaatg caagtcctcg    1740
gcccagatag acccgactcc cgtgatcgtc acctccaaca ccaacatgtg cgccgtgatt    1800
gacgggaact caacgacctt cgaacaccag cagccgttgc aagaccggat gttcaaattt    1860
gaactcaccc gccgtctgga tcatgacttt gggaaggtca ccaagcagga agtcaaagac    1920
tttttccggt gggcaaagga tcacgtggtt gaggtggagc atgaattcta cgtcaaaaag    1980
ggtggagcca agaaaagacc cgcccccagt gacgcagata taagtgagcc caaacgggtg    2040
cgcgagtcag ttgcgcagcc atcgacgtca gacgcggaag cttcgatcaa ctacgcagac    2100
aggtaccaaa acaaatgttc tcgtcacgtg ggcatgaatc tgatgctgtt tccctgcaga    2160
caatgcgaga gaatgaatca gaattcaaat atctgcttca ctcacggaca gaaagactgt    2220
ttagagtgct ttcccgtgtc agaatctcaa cccgtttctg tcgtcaaaaa ggcgtatcag    2280
aaactgtgct acattcatca tatcatggga aaggtgccag acgcttgcac tgcctgcgat    2340
ctggtcaatg tggatttgga tgactgcatc tttgaacaat aaatgactta aaccaggtat    2400
ggctgccgat ggttatcttc cagattggct cgaggacaac cttagtgaag gaattcgcga    2460
gtggtgggct ttgaaacctg gagcccctca acccaaggca aatcaacaac atcaagacaa    2520
cgctcgaggt cttgtgcttc cgggttacaa ataccttgga cccggcaacg gactcgacaa    2580
gggggagccg gtcaacgcag cagacgcggc ggccctcgag cacgacaagg cctacgacca    2640
gcagctcaag gccggagaca cccgtacct caagtacaac cacgccgacg ccgagttcca    2700
ggagcggctc aaagaagata cgtcttttgg gggcaacctc gggcgagcag tcttccaggc    2760
caaaaagagg cttcttgaac ctcttggtct ggttgaggaa gcggctaaga cggctcctgg    2820
aaagaagagg cctgtagagc agtctcctca ggaaccggac tcctccgcgg gtattggcaa    2880
atcgggtgca cagcccgcta aaaagagact caatttcggt cagactggcg acacagagtc    2940
agtcccagac cctcaaccaa tcggagaacc tcccgcagcc ccctcaggtg tgggatctct    3000
tacaatggct tcaggtggtg gcgcaccagt ggcagacaat aacgaaggtg ccgatggagt    3060
gggtagttcc tcgggaaatt ggcattgcga ttcccaatgg ctgggggaca gagtcatcac    3120
caccagcacc cgaacctggg ccctgcccac ctacaacaat cacctctaca agcaaatctc    3180
caacagcaca tctggaggat cttcaaatga caacgcctac ttcggctaca gcacccctg    3240 ggggtatttt gacttcaaca gattccactg ccacttctca ccacgtgact ggcagcgact    3300
catcaacaac aactggggat tccggcctaa gcgactcaac ttcaagctct tcaacattca    3360
ggtcaaagag gttacggaca caatggagt caagaccatc gccaataacc ttaccagcac    3420
ggtccaggtc ttcacggact cagactatca gctcccgtac gtgctcgggt cggctcacga    3480
```

```
gggctgcctc cgccgttcc cagcggacgt tttcatgatt cctcagtacg ggtatctgac    3540
gcttaatgat ggaagccagg ccgtgggtcg ttcgtccttt tactgcctgg aatatttccc   3600
gtcgcaaatg ctaagaacgg gtaacaactt ccagttcagc tacgagtttg agaacgtacc   3660
tttccatagc agctacgctc acagccaaag cctggaccga ctaatgaatc cactcatcga   3720
ccaatacttg tactatctct caaagactat taacggttct ggacagaatc aacaaacgct   3780
aaaattcagt gtggccggac ccagcaacat ggctgtccag ggaagaaact acatacctgg   3840
acccagctac cgacaacaac gtgtctcaac cactgtgact caaaacaaca acagcgaatt   3900
tgcttggcct ggagcttctt cttgggctct caatggacgt aatagcttga tgaatcctgg   3960
acctgctatg ccagccaca aagaaggaga ggaccgtttc tttcctttgt ctggatcttt    4020
aattttggc aaacaaggaa ctggaagaga caacgtggat gcggacaaag tcatgataac    4080
caacgaagaa gaaattaaaa ctactaaccc ggtagcaacg gagtcctatg acaagtggc    4140
cacaaaccac cagagtgccc aagcacaggc gcagaccggc tgggttcaaa accaaggaat   4200
acttccgggt atggtttggc aggacagaga tgtgtacctg caaggaccca tttgggccaa   4260
aattcctcac acggacggca actttcaccc ttctccgctg atgggagggt ttggaatgaa   4320
gcacccgcct cctcagatcc tcatcaaaaa cacacctgta cctgcggatc ctccaacggc   4380
cttcaacaag gacaagctga actctttcat cacccagtat tctactggcc aagtcagcgt   4440
ggagatcgag tgggagctgc agaaggaaaa cagcaagcgc tggaacccgg agatccagta   4500
cacttccaac tattacaagt ctaataatgt tgaatttgct gttaatactg aaggtgtata   4560
tagtgaaccc cgccccattg gcaccagata cctgactcgt aatctgtaat tgcttgttaa   4620
tcaataaacc gtttaatttc tagagcggcc gccccgggct gggcctcatg ggccttccgc   4680
tcactgcccg ctttccagtc gggaaacctg tcgtgccagc tgcattaaca tggtcatagc   4740
tgtttccttg cgtattgggc gctctccgct tcctcgctca ctgactcgct gcgctcggtc   4800
gttcgggtaa agcctggggt gcctaatgag caaaaggcca gcaaaaggcc aggaaccgta   4860
aaaaggccgc gttgctggcg ttttttccata ggctccgccc cctgacgag catcacaaaa   4920
atcgacgctc aagtcagagg tggcgaaacc cgacaggact ataaagatac caggcgtttc   4980
cccctggaag ctccctcgtg cgctctcctg ttccgaccct gccgcttacc ggatacctgt   5040
ccgcctttct cccttcggga agcgtggcgc tttctcatag ctcacgctgt aggtatctca   5100
gttcggtgta ggtcgttcgc tccaagctgg gctgtgtgca cgaaccccc gttcagcccg   5160
accgctgcgc cttatccggt aactatcgtc ttgagtccaa cccggtaaga cacgacttat   5220
cgccactggc agcagccact ggtaacagga ttagcagagc gaggtatgta ggcggtgcta   5280
cagagttctt gaagtggtgg cctaactacg gctacactag aagaacagta tttggtatct   5340
gcgctctgct gaagccagtt accttcggaa aaagagttgg tagctcttga tccggcaaac   5400
aaaccaccgc tggtagcggt ggtttttttg tttgcaagca gcagattacg cgcagaaaaa   5460
aaggatctca agaagatcct ttgatctttt ctacggggtc tgacgctcag tggaacgaaa   5520
actcacgtta agggattttg gtcatgagat tatcaaaaag gatcttcacc tagatccttt   5580
taaattaaaa atgaagtttt aaatcaatct aaagtatata tgagtaaact tggtctgaca   5640
gttaccaatg cttaatcagt gaggcaccta tctcagcgat ctgtctattt cgttcatcca   5700
tagttgcctg actccccgtc gtgtagataa ctacgatacg ggagggctta ccatctggcc   5760
ccagtgctgc aatgataccg cgagaaccac gctcaccggc tccagattta tcagcaataa   5820
accagccagc cggaagggcc gagcgcagaa gtggtcctgc aactttatcc gcctccatcc   5880
```

```
agtctattaa ttgttgccgg gaagctagag taagtagttc gccagttaat agtttgcgca    5940
acgttgttgc cattgctaca ggcatcgtgg tgtcacgctc gtcgtttggt atggcttcat    6000
tcagctccgg ttcccaacga tcaaggcgag ttacatgatc ccccatgttg tgcaaaaaag    6060
cggttagctc cttcggtcct ccgatcgttg tcagaagtaa gttggccgca gtgttatcac    6120
tcatggttat ggcagcactg cataattctc ttactgtcat gccatccgta agatgctttt    6180
ctgtgactgg tgagtactca accaagtcat tctgagaata gtgtatgcgg cgaccgagtt    6240
gctcttgccc ggcgtcaata cgggataata ccgcgccaca tagcagaact ttaaaagtgc    6300
tcatcattgg aaaacgttct cgggggcgaa aactctcaag gatcttaccg ctgttgagat    6360
ccagttcgat gtaacccact cgtgcaccca actgatcttc agcatctttt actttcacca    6420
gcgtttctgg gtgagcaaaa acaggaaggc aaaatgccgc aaaaaaggga ataagggcga    6480
cacggaaatg ttgaatactc atactcttcc ttttcaata ttattgaagc atttatcagg    6540
gttattgtct catgagcgga tacatatttg aatgtattta aaaaataaa caaatagggg    6600 ttccgcgcac atttccccga aaagtgccac                                      6630

<210> SEQ ID NO 5
<211> LENGTH: 6684
<212> TYPE: DNA
<213> ORGANISM: Artificial Sequence
<220> FEATURE:
<223> OTHER INFORMATION: Plasmid pRepCap9-809

<400> SEQUENCE: 5
ctaaattgta agcgttaata ttttgttaaa attcgcgtta aattttttgtt aaatcagctc      60 atttttaac caataggccg aaatcggcaa atcccttat aaatcaaaag aatagaccga     120
gatagggttg agtggccgct acagggcgct cccattcgcc attcaggctg cgcaactgtt     180
gggaagggcg tttcggtgcg ggcctcttcg ctattacgcc agctggcgaa aggggggatgt     240 gctgcaaggc gattaagttg ggtaacgcca gggttttccc agtcacgacg ttgtaaaacg     300
acggccagtg agcgcgacgt aatacgactc actatagggc gaattgaagg aaggccgtca     360
aggccgcatg atatctgagc gcgcgtaata cgactcacta tagggcgaat tgatatcggg     420
tcccggggcg ccgccgcag ggtctccatt ttgaagcggg aggtttgaac gcgcagccgc     480
catgccgggg ttttacgaga ttgtgattaa ggtccccagc gaccttgacg agcatctgcc     540
cggcatttct gacagctttg tgaactgggt ggccgagaag gaatgggagt gccgccaga     600 ttctgacatg atctgaatc tgattgagca ggcacccctg accgtggccg agaagctgca     660
gcgcgacttt ctgacggaat ggcgccgtgt gagtaaggcc ccggaggccc ttttctttgt     720
gcaatttgag aagggagaga gctacttcca catgcacgtg ctcgtggaaa ccaccggggt     780
gaaatccatg gttttgggac gtttcctgag tcagattcgc gaaaaactga ttcagagaat     840
ttaccgcgga atcgagccga cttttgccaa actggttcgc ggtcacaaaga ccagaaatgg     900 cgccggaggc gggaacaagg tggtggatga gtgctacatc cccaattact tgctccccaa     960
aacccagcct gagctccagt gggcgtggac taatatggaa cagtatttaa gcgcctgttt    1020
gaatctcacg gagcgtaaac ggttggtggc gcagcatctg acgcacgtgt cgcagacgca    1080
ggagcagaac aaagagaatc agaatcccaa ttctgatgcg ccggtgatca gatcaaaaac    1140
ttcagccagg tacatggagc tggtcgggtg gctcgtggac aagggggatta cctcggagaa    1200 gcagtggatc caggaggacc aggcctcata catctccttc aatgcggcct ccaactcgcg    1260
```

-continued

```
gtcccaaatc aaggctgcct tggacaatgc gggaaagatt atgagcctga ctaaaaccgc    1320
ccccgactac ctggtgggcc agcagcccgt ggaggacatt tccagcaatc ggatttataa    1380
aattttggaa ctaaacgggt acgatcccca atatgcggct tccgtctttc tgggatgggc    1440
cacgaaaaag ttcggcaaga ggaacaccat ctggctgttt gggcctgcaa ctaccgggaa    1500
gaccaacatc gcggaggcca tagcccacac tgtgcccttc tacgggtgcg taaactggac    1560
caatgagaac tttcccttca cgactgtgt cgacaagatg gtgatctggt gggaggaggg    1620
gaagatgacc gccaaggtcg tggagtcggc caaagccatt ctcggaggaa gcaaggtgcg    1680
cgtggaccag aaatgcaagt cctcggccca gatagacccg actcccgtga tcgtcacctc    1740
caacaccaac atgtgcgccg tgattgacgg gaactcaacg accttcgaac accagcagcc    1800
gttgcaagac cggatgttca aatttgaact cacccgccgt ctggatcatg actttgggaa    1860
ggtcaccaag caggaagtca agacttttt ccggtgggca aaggatcacg tggttgaggt    1920
ggagcatgaa ttctacgtca aaagggtgg agccaagaaa agacccgccc ccagtgacgc    1980
agatataagt gagcccaaac gggtgcgcga gtcagttgcg cagccatcga cgtcagacgc    2040
ggaagcttcg atcaactacg cagacaggta ccaaaacaaa tgttctcgtc acgtgggcat    2100
gaatctgatg ctgtttccct gcagacaatg cgagagaatg aatcagaatt caaatatctg    2160
cttcactcac ggacagaaag actgtttaga gtgctttccc gtgtcagaat ctcaacccgt    2220
ttctgtcgtc aaaaaggcgt atcagaaact gtgctacatt catcatatca tgggaaaggt    2280
gccagacgct tgcactgcct gcgatctggt caatgtggat ttggatgact gcatctttga    2340
acaataaatg acttaaacca ggtatggctg ccgatggtta tcttccagat tggctcgagg    2400
acaaccttag tgaaggaatt cgcgagtggt gggctttgaa acctggagcc cctcaaccca    2460
aggcaaatca acaacatcaa gacaacgctc gaggtcttgt gcttccgggt tacaaatacc    2520
ttggacccgg caacggactc gacaagggg agccggtcaa cgcagcagac gcggcggccc    2580
tcgagcacga caaggcctac gaccagcagc tcaaggccgg agacaacccg tacctcaagt    2640
acaaccacgc cgacgccgag ttccaggagc ggctcaaaga agatacgtct tttgggggca    2700
acctcgggcg agcagtcttc caggccaaaa agaggcttct tgaacctctt ggtctggttg    2760
aggaagcggc taagacggct cctggaaaga agaggcctgt agagcagtct cctcaggaac    2820
cggactcctc cgcgggtatt ggcaaatcgg gtgcacagcc cgctaaaaag agactcaatt    2880
tcggtcagac tggcgacaca gagtcagtcc cagaccctca accaatcgga gaacctcccg    2940 cagcccctc aggtgtggga tctcttacaa tggcttcagg tggtgcgca ccagtggcag    3000 acaataacga aggtgccgat ggagtgggta gttcctcggg aaattggcat tgcgattccc    3060
aatggctggg ggacagagtc atcaccacca gcacccgaac ctgggccctg cccacctaca    3120
acaatcacct ctacaagcaa atctccaaca gcacatctgg aggatcttca aatgacaacg    3180
cctacttcgg ctacagcacc ccctgggggt attttgactt caacagattc cactgccact    3240
tctcaccacg tgactggcag cgactcatca acaacaactg gggattccgg cctaagcgac    3300
tcaacttcaa gctcttcaac attcaggtca agaggttac ggacaacaat ggagtcaaga    3360
ccatcgccaa taccttacc agcacggtcc aggtcttcac ggactcagac tatcagctcc    3420
cgtacgtgct cgggtcggct cacgagggct gcctcccgcc gttcccagcg acgttttca    3480 tgattcctca gtacgggtat ctgacgctta atgatggaag ccaggccgtg ggtcgttcgt    3540 cctttactg cctggaatat ttcccgtcgc aaatgctaag aacgggtaac aacttccagt    3600
tcagctacga gtttgagaac gtacctttcc atagcagcta cgctcacagc caaagcctgg    3660
```

```
accgactaat gaatccactc atcgaccaat acttgtacta tctctcaaag actattaacg    3720
gttctggaca gaatcaacaa acgctaaaat tcagtgtggc cggacccagc aacatggctg    3780
tccagggaag aaactacata cctggaccca gctaccgaca acaacgtgtc tcaaccactg    3840
tgactcaaaa caacaacagc gaatttgctt ggcctggagc ttcttcttgg gctctcaatg    3900
gacgtaatag cttgatgaat cctggacctg ctatggccag ccacaaagaa ggagaggacc    3960
gtttctttcc tttgtctgga tctttaattt ttggcaaaca aggaactgga agagacaacg    4020
tggatgcgga caaagtcatg ataaccaacg aagaagaaat taaaactact aacccggtag    4080
caacggagtc ctatggacaa gtggccacaa accaccagag tgcccaagca caggcgcaga    4140
ccggctgggt tcaaaaccaa ggaatacttc cgggtatggt ttggcaggac agagatgtgt    4200
acctgcaagg acccatttgg gccaaaaatt ctcacacgga cggcaacttt caccttctc    4260 cgctgatggg agggtttgga atgaagcacc cgcctcctca gatcctcatc aaaaacacac    4320
ctgtacctgc ggatcctcca acggccttca acaaggacaa gctgaactct ttcatcaccc    4380
agtattctac tggccaagtc agcgtggaga tcgagtggga gctgcagaag gaaaacagca    4440
agcgctggaa cccggagatc cagtacactt ccaactatta caagtctaat aatgttgaat    4500
ttgctgttaa tactgaaggt gtatatagtg aaccccgccc cattggcacc agatacctga    4560
ctcgtaatct gtaattgctt gttaatcaat aaaccgttta attaggacta gtgaggtcct    4620
gtattagagg tcacgtgagt gttttgcgac attttgcgac accatgtggt cacgctgggt    4680
atttaagccc gagtgagcac gcagggtctc cattttgaag cgggaggttt gaacgcgcag    4740
ccgccctcca ttttgtctag agcggccgcc ccgggctggg cctcatgggc cttcctttca    4800
ctgcccgctt tccagtcggg aaacctgtcg tgccagctgc attaacatgg tcatagctgt    4860
ttccttgcgt attgggcgct ctccgcttcc tcgctcactg actcgctgcg ctcggtcgtt    4920
cgggtaaagc ctggggtgcc taatgagcaa aaggccagca aaaggccagg aaccgtaaaa    4980
aggccgcgtt gctggcgttt ttccataggc tccgcccccc tgacgagcat cacaaaaatc    5040
gacgctcaag tcagaggtgg cgaaacccga caggactata agataccagg cgtttccccc    5100
ctggaagctc cctcgtgcgc tctcctgttc cgaccctgcc gcttaccgga tacctgtccg    5160
cctttctccc ttcgggaagc gtggcgcttt ctcatagctc acgctgtagg tatctcagtt    5220
cggtgtaggt cgttcgctcc aagctgggct gtgtgcacga accccccgtt cagcccgacc    5280
gctgcgcctt atccggtaac tatcgtcttg agtccaaccc ggtaagacac gacttatcgc    5340
cactggcagc agccactggt aacaggatta gcagagcgag gtatgtaggc ggtgctacag    5400
agttcttgaa gtggtggcct aactacggct acactagaag aacagtattt ggtatctgcg    5460
ctctgctgaa gccagttacc ttcggaaaaa gagttggtag ctcttgatcc ggcaaacaaa    5520
ccaccgctgg tagcggtggt ttttttgttt gcaagcagca gattacgcgc agaaaaaaag    5580
gatctcaaga agatcctttg atcttttcta cggggtctga cgctcagtgg aacgaaaact    5640
cacgttaagg gattttggtc atgagattat caaaaaggat cttcacctag atccttttaa    5700
attaaaaatg aagttttaaa tcaatctaaa gtatatatga gtaaacttgg tctgacagtt    5760
attagaaaaa ttcatccagc agacgataaa acgcaatacg ctggctatcc ggtgccgcaa    5820
tgccatacag caccagaaaa cgatccgccc attcgccgcc cagttcttcc gcaatatcac    5880
gggtggccag cgcaatatcc tgataacgat ccgccacgcc cagacggccg caatcaataa    5940
agccgctaaa acggccattt tccaccataa tgttcggcag gcacgcatca ccatgggtca    6000
```

| | |
|---|---|
| ccaccagatc ttcgccatcc ggcatgctcg ctttcagacg cgcaaacagc tctgccggtg | 6060 |
| ccaggccctg atgttcttca tccagatcat cctgatccac caggcccgct tccatacggg | 6120 |
| tacgcgcacg ttcaatacga tgtttcgcct gatgatcaaa cggacaggtc gccgggtcca | 6180 |
| gggtatgcag acgacgcatg gcatccgcca taatgctcac ttttctgcc ggcgccagat | 6240 |
| ggctagacag cagatcctga cccggcactt cgcccagcag cagccaatca cggcccgctt | 6300 |
| cggtcaccac atccagcacc gccgcacacg gaacaccggt ggtggccagc agctcagac | 6360 |
| gcgccgcttc atcctgcagc tcgttcagcg caccgctcag atcggttttc acaaacagca | 6420 |
| ccggacgacc ctgcgcgctc agacgaaaca ccgccgcatc agagcagcca atggtctgct | 6480 |
| gcgcccaatc atagccaaac agacgttcca cccacgctgc cgggctaccc gcatgcaggc | 6540 |
| catcctgttc aatcatactc ttccttttc aatattattg aagcattat cagggttatt | 6600 |
| gtctcatgag cggatacata tttgaatgta tttagaaaaa taaacaaata ggggttccgc | 6660 |
| gcacatttcc ccgaaaagtg ccac | 6684 |

<210> SEQ ID NO 6
<211> LENGTH: 11584
<212> TYPE: DNA
<213> ORGANISM: Artificial Sequence
<220> FEATURE:
<223> OTHER INFORMATION: Plasmid pAdHelper861

<400> SEQUENCE: 6

| | |
|---|---|
| ctaaattgta agcgttaata ttttgttaaa attcgcgtta aatttttgtt aaatcagctc | 60 |
| attttttaac caataggccg aaatcggcaa aatcccttat aaatcaaaag aatagaccga | 120 |
| gatagggttg agtggccgct acagggcgct cccattcgcc attcaggctg cgcaactgtt | 180 |
| gggaagggcg tttcggtgcg ggcctcttcg ctattacgcc agctggcgaa agggggatgt | 240 |
| gctgcaaggc gattaagttg gtaacgccca gggttttccc agtcacgacg ttgtaaaacg | 300 |
| acggccagtg agcgcgacgt aatacgactc actatagggc gaattgaagg aaggccgtca | 360 |
| aggccgcatg cggccgcagt actatccgta gatgtacctg acatccagg tgatgccggc | 420 |
| ggcggtggtg gaggcgcgcg gaaagtcgcg gacgcggttc cagatgttgc gcagcggcaa | 480 |
| aaagtgctcc atggtcggga cgctctggcc ggtcaggcgc gcgcaatcgt tgacgctcta | 540 |
| gaccgtgcaa aaggagagcc tgtaagcggg cactcttccg tggtctggtg gataaattcg | 600 |
| caagggtatc atggcggacg accggggttc gagccccgta tccggccgtc gccgtgatc | 660 |
| catgcggtta ccgcccgcgt gtcgaaccca ggtgtgcgac gtcagacaac gggggagtgc | 720 |
| tccttttggc ttccttccag gcgcggcggc tgctgcgcta gctttttgg ccactggccg | 780 |
| cgcgcagcgt aagcggttag ctggaaagc gaaagcatta agtggctcgc tccctgtagc | 840 |
| cggagggtta tttttccaagg gttgagtcgc gggaccccg gttcgagtct cggaccggcc | 900 |
| ggactgcggc gaacggggt ttgcctcccc gtcatgcaag ccccgcttg caaattcctc | 960 |
| cggaaacagg gacgagcccc tttttgctt ttcccagatg catccggtgc tgcggcagat | 1020 |
| gcgccccct cctcagcagc ggcaagagca agagcagcgg cagacatgca gggcaccctc | 1080 |
| ccctcctcct accgcgtcag gaggggcgac atcctgcga ggtacccaac tccatgctca | 1140 |
| acagtcccca ggtacagccc accctgcgtc gcaaccagga cagctctac agcttcctgg | 1200 |
| agcgccactc gccctacttc cgcagccaca gtgcgcagat taggagcgcc acttcttttt | 1260 |
| gtcacttgaa aaacatgtaa aaataatgta ctagagacac tttcaataaa ggcaaatgct | 1320 |
| tttatttgta cactctcggg tgattattta ccccacccct tgccgtctgc gccgtttaaa | 1380 |

```
aatcaaaggg gttctgccgc gcatcgctat gcgccactgg cagggacacg ttgcgatact    1440
ggtgtttagt gctccactta aactcaggca caaccatccg cggcagctcg gtgaagtttt    1500
cactccacag gctgcgcacc atcaccaacg cgtttagcag gtcgggcgcc gatatcttga    1560
agtcgcagtt ggggcctccg ccctgcgcgc gcgagttgcg atacacaggg ttgcagcact    1620
ggaacactat cagcgccggg tggtgcacgc tggccagcac gctcttgtcg gagatcagat    1680
ccgcgtccag gtcctccgcg ttgctcaggg cgaacggagt caactttggt agctgccttc    1740
ccaaaaaggg cgcgtgccca ggctttgagt tgcactcgca ccgtagtggc atcaaaaggt    1800
gaccgtgccc ggtctgggcg ttaggataca gcgcctgcat aaaagccttg atctgcttaa    1860
aagccacctg agcctttgcg ccttcagaga agaacatgcc gcaagacttg ccggaaaact    1920
gattggccgg acaggccgcg tcgtgcacgc agcaccttgc gtcggtgttg agatctgca    1980 ccacatttcg gccccaccgg ttcttcacga tcttggcctt gctagactgc tccttcagcg    2040
cgcgctgccc gttttcgctc gtcacatcca tttcaatcac gtgctcctta tttatcataa    2100
tgcttccgtg tagacactta agctcgcctt cgatctcagc gcagcggtgc agccacaacg    2160
cgcagcccgt gggctcgtga tgcttgtagg tcacctctgc aaacgactgc aggtacgcct    2220
gcaggaatcg ccccatcatc gtcacaaagg tcttgttgct ggtgaaggtc agctgcaacc    2280
cgcggtgctc ctcgttcagc caggtcttgc atacggccgc cagagcttcc acttggtcag    2340
gcagtagttt gaagttcgcc tttagatcgt tatccacgtg gtacttgtcc atcagcgcgc    2400
gcgcagcctc catgcccttc tcccacgcag acacgatcgg cacactcagc gggttcatca    2460
ccgtaatttc actttccgct tcgctgggct cttcctcttc ctcttgcgtc cgcataccac    2520
gcgccactgg gtcgtcttca ttcagccgcc gcactgtgcg cttacctcct ttgccatgct    2580
tgattagcac cggtgggttg ctgaaaccca ccatttgtag cgccacatct tctctttctt    2640
cctcgctgtc cacgattacc tctggtgatg gcgggcgctc gggcttggga aagggcgct    2700 tcttttcctt cttgggcgca atggccaaat ccgccgccga ggtcgatggc cgcgggctgg    2760
gtgtgcgcgg caccagcgcg tcttgtgatg agtcttcctc gtcctcggac tcgatacgcc    2820
gcctcatccg ctttttggg ggcgcccggg gaggcggcgg cgacggggac ggggacgaca    2880
cgtcctccat ggttggggga cgtcgcgccg caccgcgtcc gcgctcgggg gtggtttcgc    2940
gctgctcctc ttcccgactg gccatttcct tctcctatag gcagaaaaag atcatggagt    3000
cagtcgagaa gaaggacagc ctaaccgccc cctctgagtt cgccaccacc gcctccaccg    3060
atgccgccaa cgcgcctacc accttccccg tcgaggcacc cccgcttgag gaggaggaag    3120
tgattatcga gcaggaccca ggttttgtaa gcgaagacga cgaggaccgc tcagtaccaa    3180
cagaggataa aaagcaagac caggacaacg cagaggcaaa cgaggaacaa gtcgggcggg    3240
gggacgaaag gcatggcgac tacctagatg tgggagacga cgtgctgttg aagcatctgc    3300
agcgccagtg cgccattatc tgcgacgcgt tgcaagagcg cagcgatgtg cccctcgcca    3360
tagcggatgt cagccttgcc tacgaacgcc acctattctc accgcgcgta ccccccaaac    3420
gccaagaaaa cggcacatgc gagcccaacc cgcgcctcaa cttctacccc gtatttgccg    3480
tgccagaggt gcttgccacc tatcacatct tttccaaaa ctgcaagata ccctatcct    3540 gccgtgccaa ccgcagccga gcggacaagc agctggcctt gcggcagggc gctgtcatac    3600
ctgatatcgc ctcgctcaac gaagtgccaa aaatctttga gggtcttgga cgcgacgaga    3660
agcgcgcggc aaacgctctg caacaggaaa acagcgaaaa tgaaagtcac tctggagtgt    3720
```

```
tggtggaact cgagggtgac aacgcgcgcc tagccgtact aaaacgcagc atcgaggtca    3780
cccactttgc ctaccggca cttaacctac cccccaaggt catgagcaca gtcatgagtg    3840
agctgatcgt gcgccgtgcg cagcccctgg agagggatgc aaatttgcaa gaacaaacag    3900
aggagggcct acccgcagtt ggcgacgagc agctagcgcg ctggcttcaa acgcgcgagc    3960
ctgccgactt ggaggagcga cgcaaactaa tgatggccgc agtgctcgtt accgtggagc    4020
ttgagtgcat gcagcggttc tttgctgacc cggagatgca cgcaagcta gaggaaacat    4080
tgcactacac ctttcgacag ggctacgtac gccaggcctg caagatctcc aacgtggagc    4140
tctgcaacct ggtctcctac cttggaattt tgcacgaaaa ccgccttggg caaaacgtgc    4200
ttcattccac gctcaagggc gaggcgcgcc gcgactacgt ccgcgactgc gtttacttat    4260
ttctatgcta cacctggcag acggccatgg gcgtttggca gcagtgcttg gaggagtgca    4320
acctcaagga gctgcagaaa ctgctaaagc aaaacttgaa ggacctatgg acggccttca    4380
acgagcgctc cgtggccgcg cacctggcgg acatcatttt ccccgaacgc ctgcttaaaa    4440
ccctgcaaca gggtctgcca gacttcacca gtcaaagcat gttgcagaac tttaggaact    4500
ttatcctaga gcgctcagga atcttgcccg ccacctgctg tgcacttcct agcgactttg    4560
tgcccattaa gtaccgcgaa tgccctccgc gctttgggg ccactgctac cttctgcagc    4620
tagccaacta ccttgcctac cactctgaca taatggaaga cgtgagcggt gacggtctac    4680
tggagtgtca ctgtcgctgc aacctatgca ccccgcaccg ctccctggtt tgcaattcgc    4740
agctgcttaa cgaaagtcaa attatcggta cctttgagct gcagggtccc tcgcctgacg    4800
aaaagtccgc ggctccgggg ttgaaactca ctccggggct gtggacgtcg gcttaccttc    4860
gcaaatttgt acctgaggac taccacgccc acgagattag gttctacgaa gaccaatccc    4920
gcccgccaaa tgcggagctt accgcctgcg tcattaccca gggccacatt cttggccaat    4980
tgcaagccat caacaaagcc cgccaagagt ttctgctacg aaagggacgg ggggtttact    5040
tggaccccca gtccggcgag gagctcaacc caatccccc ccgccgcag ccctatcagc    5100
agcagccgcg ggcccttgct tcccaggatg gcacccaaaa agaagctgca gctgccgccg    5160
ccacccacgg acgaggagga atactgggac agtcaggcag aggaggtttt ggacgaggag    5220
gaggaggaca tgatggaaga ctgggagagc ctagacgagg aagcttccga ggtcgaagag    5280
gtgtcagacg aaaacaccgtc accctcggtc gcattcccct cgccggcgcc ccagaaatcg    5340
gcaaccggtt ccagcatggc tacaacctcc gctcctcagg cgccgccggc actgcccgtt    5400
cgccgaccca accgtagatg ggacaccact ggaaccaggg ccggtaagtc caagcagccg    5460
ccgccgttag cccaagagca acaacagcgc caaggctacc gctcatggcg cgggcacaag    5520
aacgccatag ttgcttgctt gcaagactgt ggggcaaca tctccttcgc ccgccgcttt    5580
cttctctacc atcacggcgt ggccttcccc cgtaacatcc tgcattacta ccgtcatctc    5640
tacagcccat actgcaccgg cggcagcggc agcggcagca acagcagcgg ccacacagaa    5700
gcaaaggcga ccggatagca agactctgac aaagcccaag aaatccacag cggcggcagc    5760
agcaggagga ggagcgctgc gtctggcgcc caacgaaccc gtatcgaccc gcgagcttag    5820
aaacaggatt tttcccactc tgtatgctat atttcaacag agcaggggcc aagaacaaga    5880
gctgaaaata aaaaacaggt ctctgcgatc cctcacccgc agctgcctgt atcacaaaag    5940
cgaagatcag cttcggcgca cgctggaaga cgcggaggct ctcttcagta aatactgcgc    6000
gctgactctt aaggactagt ttcgcgccct ttctcaaatt taagcgcgaa aactacgtca    6060
tctccagcgg ccacacccgg cgccagcacc tgtcgtcagc gccattatga gcaaggaaat    6120
```

```
tcccacgccc tacatgtgga gttaccagcc acaaatggga cttgcggctg gagctgccca   6180
agactactca acccgaataa actacatgag cgcgggaccc cacatgatat cccgggtcaa   6240
cggaatccgc gcccaccgaa accgaattct cttggaacag gcggctatta ccaccacacc   6300
tcgtaataac cttaatcccc gtagttggcc cgctgccctg tgtaccagg aaagtcccgc    6360 tcccaccact gtggtacttc ccagagacgc ccaggccgaa gttcagatga ctaactcagg   6420
ggcgcagctt gcgggcggct ttcgtcacag ggtgcggtcg cccgggtcgc gagtttaaac   6480
tacacaggaa acaggagaca caactccaag tgcatactct atgtcatttt catgggactg   6540
gtctggccac aactcattta tgaaatatt tgccacatcc tcttacactt tttcatacat     6600
tgcccaagaa taaagaatcg tttgtgttat gtttcaacgt gtttattttt caattgcaga   6660
aaatttcaag tcatttttca ttcagtagta tagccccacc accacatagc ttatacagat   6720
caccgtacct taatcaaact cacagaaccc tagtattcaa cctgccacct ccctcccaac   6780
acacagagta cacagtcctt tctccccggc tggccttaaa aagcatcata tcatgggtaa   6840
cagacatatt cttaggtgtt atattccaca cggtttcctg tcgagccaaa cgctcatcag   6900
tgatattaat aaactccccg ggcagctcac ttaagttcat gtcgctgtcc agctgctgag   6960
ccacaggctg ctgtccaact tgcggttgct taacgggcgg cgaaggagaa gtccacgcct   7020
acatgggggt agagtcataa tcgtgcatca ggatagggcg gtggtgctgc agcagcgcgc   7080
gaataaactg ctgccgccgc cgctccgtcc tgcaggaata caacatggca gtggtctcct   7140
cagcgatgat tcgcaccgcc cgcagcataa ggcgccttgt cctccgggca cagcagcgca   7200
ccctgatctc acttaaatca gcacagtaac tgcagcacag caccacaata ttgttcaaaa   7260
tcccacagtg caaggcgctg tatccaaagc tcatggcggg gaccacagaa cccacgtggc   7320
catcatacca caagcgcagg tagattaagt ggcgacccct cataaacacg ctggacataa   7380
acattacctc ttttggcatg ttgtaattca ccacctcccg gtaccatata aacctctgat   7440
taaacatggc gccatccacc accatcctaa accagctggc caaaacctgc ccgccggcta   7500
tacactgcag ggaaccggga ctggaacaat gacagtggag agcccaggac tcgtaaccat   7560
ggatcatcat gctcgtcatg atatcaatgt tggcacaaca caggcacacg tgcatacact   7620
tcctcaggat tacaagctcc tcccgcgtta gaaccatatc ccagggaaca acccattcct   7680
gaatcagcgt aaatcccaca ctgcagggaa gacctcgcac gtaactcacg ttgtgcattg   7740
tcaaagtgtt acattcgggc agcagcggat gatcctccag tatggtagcg cgggtttctg   7800
tctcaaaagg aggtagacga tccctactgt acggagtgcg ccgagacaac cgagatcgtg   7860
ttggtcgtag tgtcatgcca aatggaacgc cggacgtagt catatttcct gaagcaaaac   7920
caggtgcggg cgtgacaaac agatctgcgt ctccggtctc gccgcttaga tcgctctgtg   7980
tagtagttgt agtatatcca ctctctcaaa gcatccaggc gcccctggc ttcgggttct    8040 atgtaaactc cttcatgcgc cgctgccctg ataacatcca ccaccgcaga ataagccaca   8100
cccagccaac ctacacattc gttctgcgag tcacacacgg gaggagcggg aagagctgga   8160
agaaccatgt ttttttttt attccaaaag attatccaaa acctcaaaat gaagatctat    8220
taagtgaacg cgctcccctc cggtggcgtg gtcaaactct acagccaaag aacagataat   8280
ggcatttgta agatgttgca caatggcttc caaaaggcaa acggccctca cgtccaagtg   8340
gacgtaaagg ctaaacccct cagggtgaat ctcctctata aacattccag caccttcaac   8400
catgcccaaa taattctcat ctcgccacct tctcaatata tctctaagca aatcccgaat   8460
```

```
attaagtccg gccattgtaa aaatctgctc cagagcgccc tccaccttca gcctcaagca    8520
gcgaatcatg attgcaaaaa ttcaggttcc tcacagacct gtataagatt caaaagcgga    8580
acattaacaa aaataccgcg atcccgtagg tcccttcgca gggccagctg aacataatcg    8640
tgcaggtctg cacggaccag cgcggccact tccccgccag gaaccatgac aaaagaaccc    8700
acactgatta tgacacgcat actcggagct atgctaacca gcgtagcccc gatgtaagct    8760
tgttgcatgg gcggcgatat aaaatgcaag gtgctgctca aaaaatcagg caaagcctcg    8820
cgcaaaaaag aaagcacatc gtagtcatgc tcatgcagat aaaggcaggt aagctccgga    8880
accaccacag aaaagacac cattttctc tcaaacatgt ctgcgggttt ctgcataaac     8940
acaaaataaa ataacaaaaa aacatttaaa cattagaagc ctgtcttaca acaggaaaaa    9000
caacccttat aagcataaga cggactacgg ccatgccggc gtgaccgtaa aaaactggt    9060 caccgtgatt aaaaagcacc accgacagct cctcggtcat gtccggagtc ataatgtaag    9120
actcggtaaa cacatcaggt tgattcacat cggtcagtgc taaaaagcga ccgaaatagc    9180
ccgggggaat acatacccgc aggcgtagag acaacattac agcccccata ggaggtataa    9240
caaaattaat aggagagaaa aacacataaa cacctgaaaa accctcctgc ctaggcaaaa    9300
tagcaccctc ccgctccaga acaacataca gcgcttccac agcggcagcc ataacagtca    9360
gccttaccag taaaaagaa aacctattaa aaaacacca ctcgacacgg caccagctca     9420
atcagtcaca gtgtaaaaaa gggccaagtg cagagcgagt atatatagga ctaaaaatg    9480 acgtaacggt taaagtccac aaaaaacacc cagaaaaccg cacgcgaacc tacgcccaga   9540
aacgaaagcc aaaaaaccca caacttcctc aaatcgtcac ttccgttttc ccacgttacg    9600
taacttccca ttttaagaaa actacaattc ccaacacata caagttactc cgccctaaaa    9660
cgttaacgcg gccgctgggc cctcatgggc cttcctttca ctgcccgctt tccagtcggg    9720
aaacctgtcg tgccagctgc attaacatgg tcatagctgt ttccttgcgt attgggcgct    9780
ctccgcttcc tcgctcactg actcgctgcg ctcggtcgtt cgggtaaagc ctggggtgcc    9840
taatgagcaa aaggccagca aaaggccagg aaccgtaaaa aggccgcgtt gctggcgttt    9900
ttccataggc tccgcccccc tgacgagcat cacaaaaatc gacgctcaag tcagaggtgg    9960
cgaaacccga caggactata agataccag gcgtttcccc ctggaagctc cctcgtgcgc    10020
tctcctgttc cgaccctgcc gcttaccgga tacctgtccg cctttctccc ttcgggaagc    10080
gtggcgcttt ctcatagctc acgctgtagg tatctcagtt cggtgtaggt cgttcgctcc    10140
aagctgggct gtgtgcacga accccccgtt cagcccgacc gctgcgcctt atccggtaac    10200
tatcgtcttg agtccaaccc ggtaagacac gacttatcgc cactggcagc agccactggt    10260
aacaggatta gcagagcgag gtatgtaggc ggtgctacag agttcttgaa gtggtggcct    10320
aactacggct acactagaag aacagtattt ggtatctgcg ctctgctgaa gccagttacc    10380
ttcggaaaaa gagttggtag ctcttgatcc ggcaaacaaa ccaccgctgg tagcggtggt    10440
ttttttgttt gcaagcagca gattacgcgc agaaaaaaag gatctcaaga agatcctttg    10500
atcttttcta cggggtctga cgctcagtgg aacgaaaact cacgttaagg gattttggtc    10560
atgagattat caaaaaggat cttcacctag atccttttaa attaaaaatg aagttttaaa    10620
tcaatctaaa gtatatatga gtaaacttgg tctgacagtt attagaaaaa ttcatccagc    10680
agacgataaa acgcaatacg ctggctatcc ggtgccgcaa tgccatacag caccagaaaa    10740
cgatccgccc attcgccgcc cagttcttcc gcaaatcac gggtggccag cgcaatatcc    10800
tgataacgat ccgccacgcc cagacggccg caatcaataa agccgctaaa acggccattt    10860
```

```
tccaccataa tgttcggcag gcacgcatca ccatgggtca ccaccagatc ttcgccatcc    10920
ggcatgctcg ctttcagacg cgcaaacagc tctgccggtg ccaggccctg atgttcttca    10980
tccagatcat cctgatccac caggcccgct tccatacggg tacgcgcacg ttcaatacga    11040
tgtttcgcct gatgatcaaa cggacaggtc gccgggtcca gggtatgcag acgacgcatg    11100
gcatccgcca taatgctcac ttttctgcc ggcgccagat ggctagacag cagatcctga    11160
cccggcactt cgcccagcag cagccaatca cggcccgctt cggtcaccac atccagcacc    11220
gccgcacacg gaacaccggt ggtggccagc cagctcagac gcgccgcttc atcctgcagc    11280
tcgttcagcg caccgctcag atcggttttc acaaacagca ccggacgacc ctgcgcgctc    11340
agacgaaaca ccgccgcatc agagcagcca atggtctgct gcgcccaatc atagccaaac    11400
agacgttcca cccacgctgc cgggctaccc gcatgcaggc catcctgttc aatcatactc    11460
ttcctttttc aatattattg aagcatttat cagggttatt gtctcatgag cggatacata    11520
tttgaatgta tttagaaaaa taaacaaata ggggttccgc gcacatttcc ccgaaaagtg    11580
ccac                                                                11584
```